(12) United States Patent
Ben-Tzvi et al.

(10) Patent No.: US 12,318,156 B2
(45) Date of Patent: Jun. 3, 2025

(54) EXTENSIBLE CONTINUUM MANIPULATOR

(71) Applicant: VIRGINIA TECH INTELLECTUAL PROPERTIES, INC., Blacksburg, VA (US)

(72) Inventors: Pinhas Ben-Tzvi, Blacksburg, VA (US); Yujiong Liu, Blacksburg, VA (US)

(73) Assignee: VIRGINIA TECH INTELLECTUAL PROPERTIES, INC., Blacksburg, VA (US)

(*) Notice: Subject to any disclaimer, the term of this patent is extended or adjusted under 35 U.S.C. 154(b) by 343 days.

(21) Appl. No.: 17/996,712

(22) PCT Filed: May 27, 2021

(86) PCT No.: PCT/US2021/034564
§ 371 (c)(1),
(2) Date: Oct. 20, 2022

(87) PCT Pub. No.: WO2021/243047
PCT Pub. Date: Dec. 2, 2021

(65) Prior Publication Data
US 2023/0233274 A1 Jul. 27, 2023

Related U.S. Application Data

(60) Provisional application No. 63/032,200, filed on May 29, 2020.

(51) Int. Cl.
*B25J 9/06* (2006.01)
*A61B 34/30* (2016.01)
(Continued)

(52) U.S. Cl.
CPC ............... *A61B 34/30* (2016.02); *B25J 9/065* (2013.01); *B25J 9/1035* (2013.01); *B25J 9/104* (2013.01);
(Continued)

(58) Field of Classification Search
CPC .... A61B 34/30; A61B 2034/301; B25J 9/065; B25J 9/1035; B25J 9/104; B25J 18/02
See application file for complete search history.

(56) References Cited

U.S. PATENT DOCUMENTS 10,959,797 B2 * 3/2021 Licht .................... A61B 34/76
2013/0090763 A1 4/2013 Simaan et al.
(Continued)

OTHER PUBLICATIONS

International Search Report and Written Opinion for PCTUS2021034564 mailed Nov. 4, 2021.

*Primary Examiner* — Kira Nguyen
(74) *Attorney, Agent, or Firm* — Jonathan A. Paulis; Perilla Knox & Hildebrandt LLP

(57) ABSTRACT

Various embodiments for a continuum manipulator are described for use in robotic surgical systems or other desired applications. The continuum manipulator includes an extensible continuum manipulator (ECM) body comprising a plurality of subsegments serially connected to one another. Adjacent ones of the subsegments are coupled by rack-and-pinion transmission sets that are configured to propagate subsegment motion to downstream ones of the subsegments. A multi-chain flexible parallel mechanism is provided in each of the subsegments that is configured to generate a desired spatial bending and extension mobility for each of the subsegments.

20 Claims, 17 Drawing Sheets

(51) Int. Cl.
 *B25J 9/10* (2006.01)
 *B25J 18/02* (2006.01)
(52) U.S. Cl.
 CPC ......... *B25J 18/02* (2013.01); *A61B 2034/301* (2016.02)

(56) References Cited

U.S. PATENT DOCUMENTS

| | | |
|---|---|---|
| 2014/0330432 A1 | 11/2014 | Simaan et al. |
| 2015/0100065 A1* | 4/2015 | Zinn ................ A61B 34/30 606/130 |
| 2017/0049298 A1* | 2/2017 | Hunter .............. A61B 5/067 |
| 2018/0154515 A1* | 6/2018 | Norton .............. B25J 18/06 |
| 2019/0231452 A1 | 8/2019 | Xu et al. |
| 2019/0366533 A1 | 12/2019 | Ben-Tzvi et al. |
| 2020/0188042 A1* | 6/2020 | Dong ................ B25J 9/065 |
| 2021/0045821 A1* | 2/2021 | Yang ................ A61B 1/008 |

\* cited by examiner

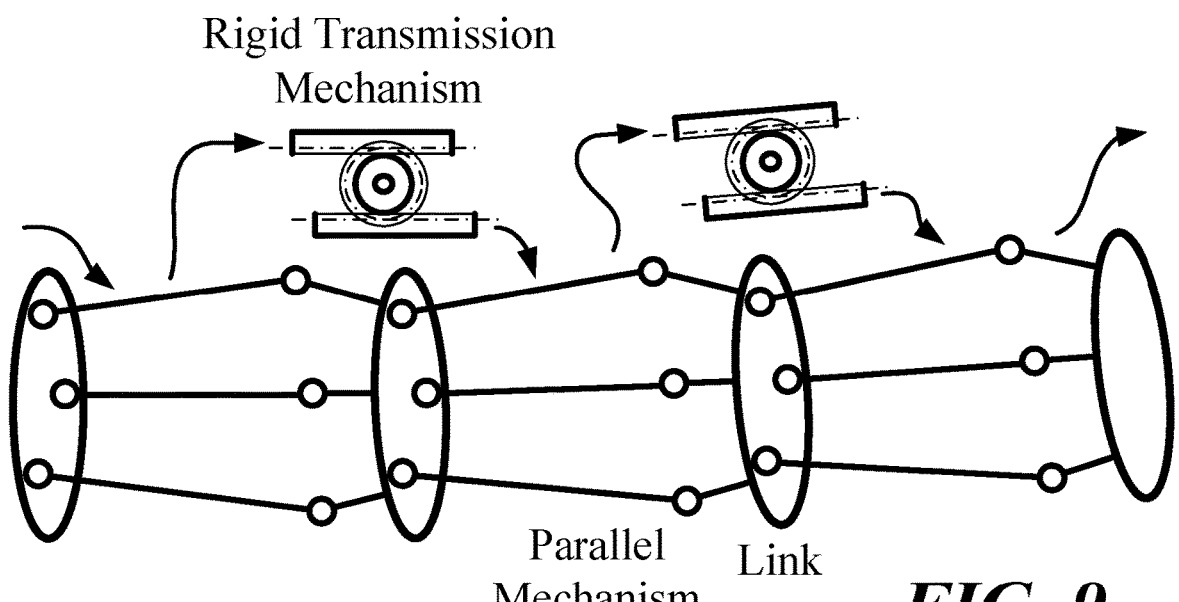
FIG. 9
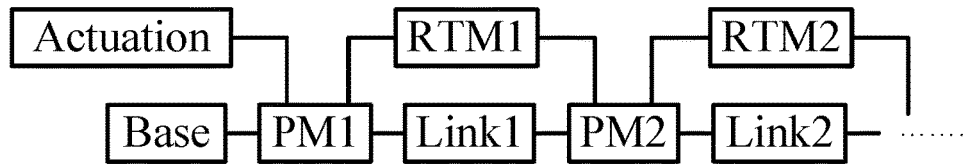

EXTENSIBLE CONTINUUM MANIPULATOR

CROSS-REFERENCE TO RELATED APPLICATION

This application is a 35 U.S.C. § 371 national stage patent application of Patent Cooperation Treaty application number PCT/US2021/034564, filed May 27, 2021, and titled "EXTENSIBLE CONTINUUM MANIPULATOR," which claims the benefit of and priority to U.S. Provisional Patent Application No. 63/032,200 filed May 29, 2020, entitled "EXTENSIBLE CONTINUUM MANIPULATOR USING FLEXIBLE PARALLEL MECHANISM AND RIGID MOTION TRANSMISSION," the entire contents of both of which applications are hereby incorporated herein by reference.

FEDERALLY SPONSORED RESEARCH STATEMENT

This invention was made with government support under Grant No. 1906727 awarded by the National Science Foundation. The government has certain rights in the invention.

BACKGROUND

Inspired by nature, continuum robots and, more specifically, continuum manipulators, are developed to achieve animal-like properties. These properties are critical for certain applications that require passive compliance, for instance, medical robots that need to interact with human tissues, manipulation robots that need to handle fragile objects, or exploration robots that need to go through complex and potentially narrow passages. Traditional solutions for this kind of robots focus on using deformable materials (e.g., an elastic backbone) and deformable actuation (e.g., tendon or rod driven). Existing examples using this technology include the elephant trunk robot, tentacle robot, and the distal dexterity unit (DDU) surgical robot, etc.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 9 and 10 are kinematic schematic diagrams of the extensible continuum manipulator and rack-and-pinion sets thereof according to various embodiments of the present disclosure.

DETAILED DESCRIPTION

Various embodiments for an extensible continuum manipulator (ECM) are described. Existing continuum manipulators include elephant trunk robotic devices, tentacle robotic devices, distal dexterity units (DDUs), and so forth. Other robotic devices include hyper-redundant structures, which are not continuum devices, but behave like one. An extensible continuum manipulator (ECM) as described herein has specific advantages over non-extensible counterpart robotic devices. For instance, in certain applications, such as minimally invasive surgery or tube inspection, base motion might be limited or impossible.

Extensibility of the ECM described herein achieves a robotic device having more dexterous manipulation and a larger workspace. Existing continuum robot designs achieve extensibility mainly through artificial muscles (e.g., pneumatics), extensible backbones, concentric tubes, base extensions, and so forth. Rather, embodiments for the continuum robotic device described herein achieves additional motions and degrees-of-freedom by taking advantage of a rigid coupling hybrid mechanism (RCHM) and/or a flexible parallel mechanism, as will be described.

More specifically, a rack-and-pinion set is described that is capable of transmitting motion of an i-th subsegment to drive an (i+1)-th subsegment. In some embodiments, a six-chain flexible parallel mechanism is described that may generate desired spatial bending and extension mobility for each subsegment. To this end, the extensible continuum manipulator described herein is able to achieve tail-like spatial bending and worm-like extension at the same time.

Example embodiments will now be described more fully with reference to the accompanying drawings. However, the example embodiments may be implemented in various forms, and should not be construed as being limited to the embodiments set forth herein. Rather, these embodiments are provided so that the present disclosure will be comprehensive and fully convey the concept of the example embodiments.

Referring now to FIGS. 1-5, various views of an example of a robotic system 100 are shown in accordance with various embodiments. The robotic system 100 may include one or more actuators 102 and a continuum manipulator 104. The one or more actuators 102 may include, for example, one or more linear actuators that drive the continuum manipulator 104 using horizontal or lateral force, as will be described. Other suitable driving mechanisms may be employed.

Figure 1:
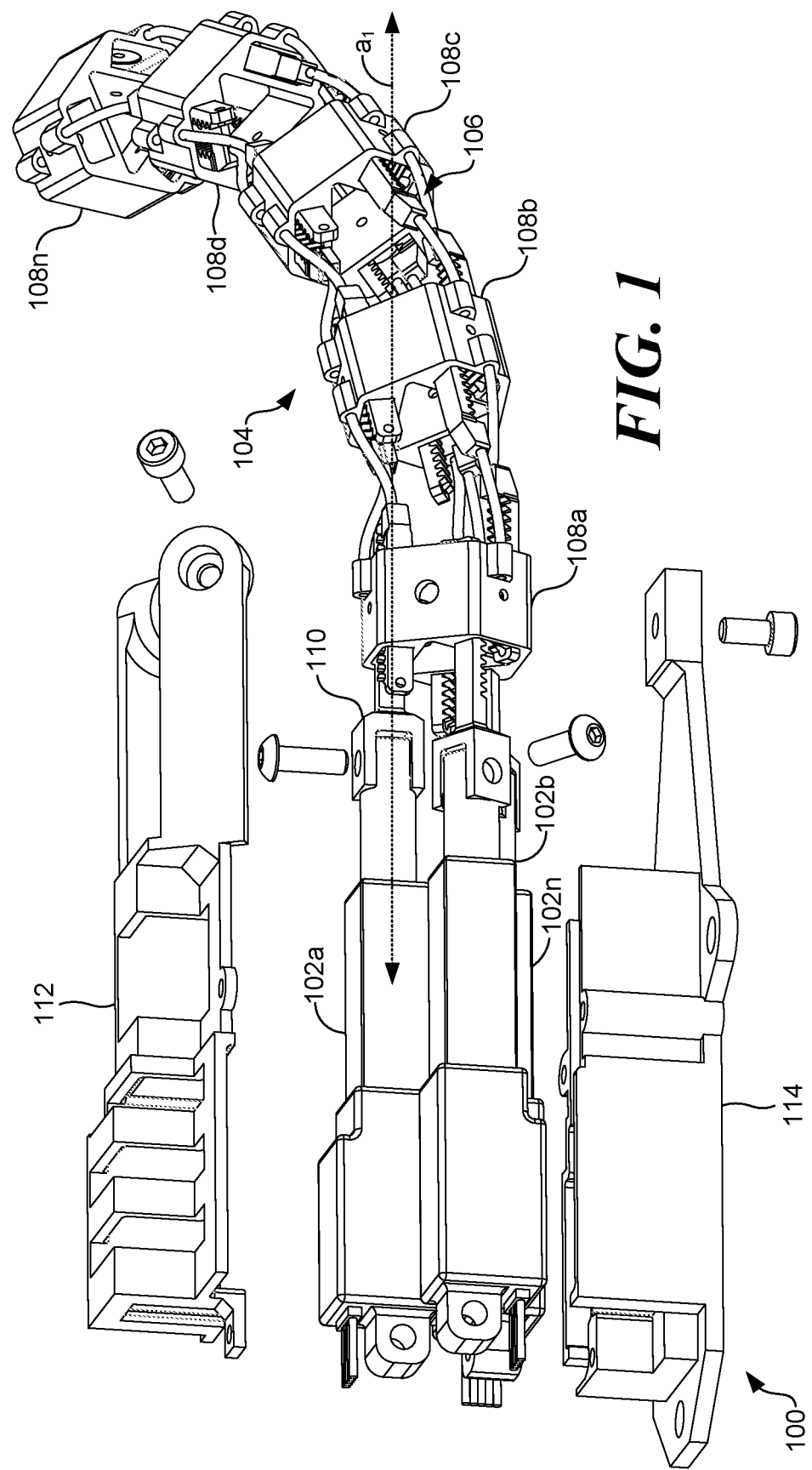
FIG. 1 is an exploded perspective view of a robotic system having an extensible continuum manipulator according to various embodiments of the present disclosure.
Figure 2:
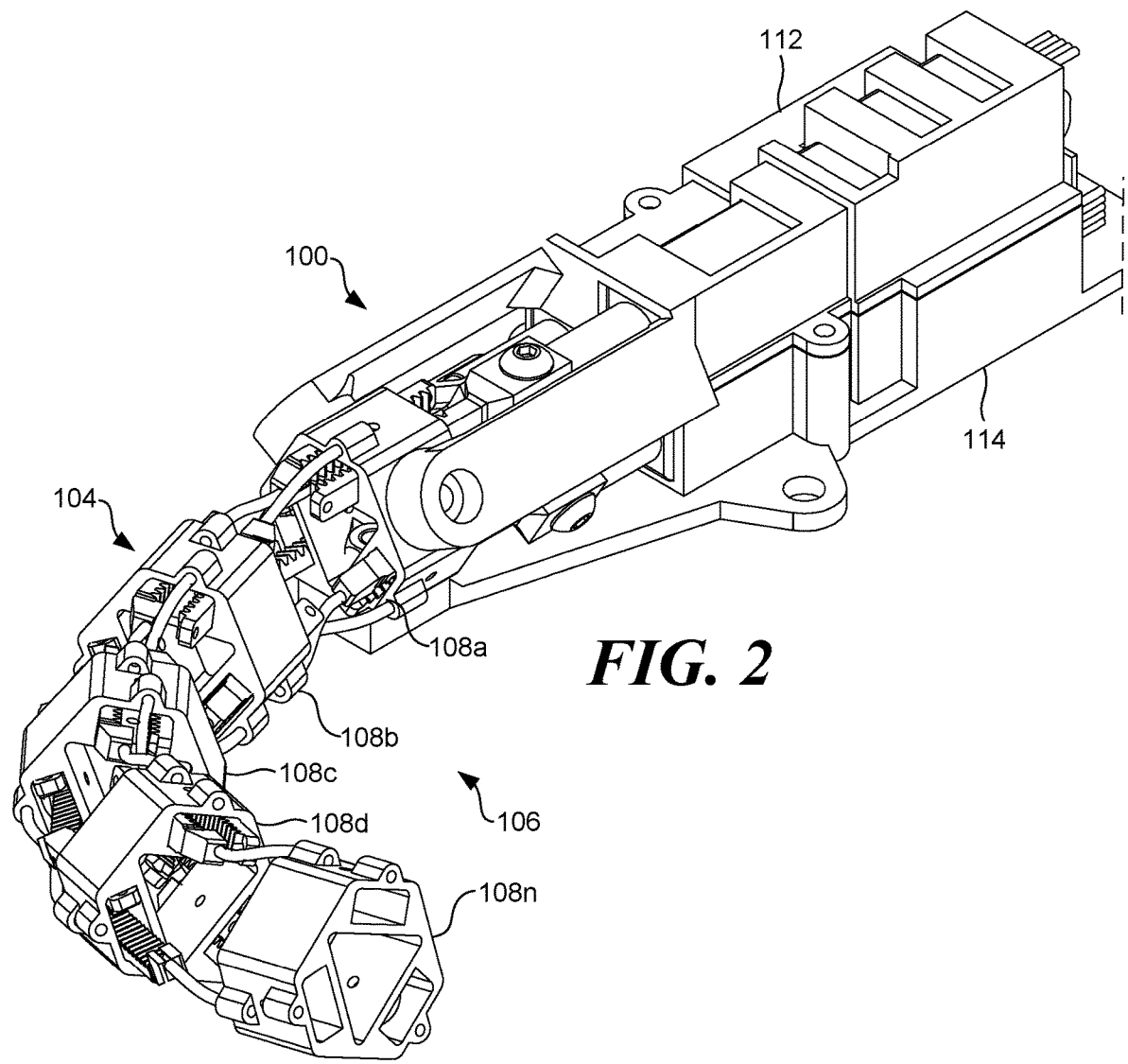
FIG. 2 is a top perspective view of the robotic system having the extensible continuum manipulator according to various embodiments of the present disclosure.
Figure 3:
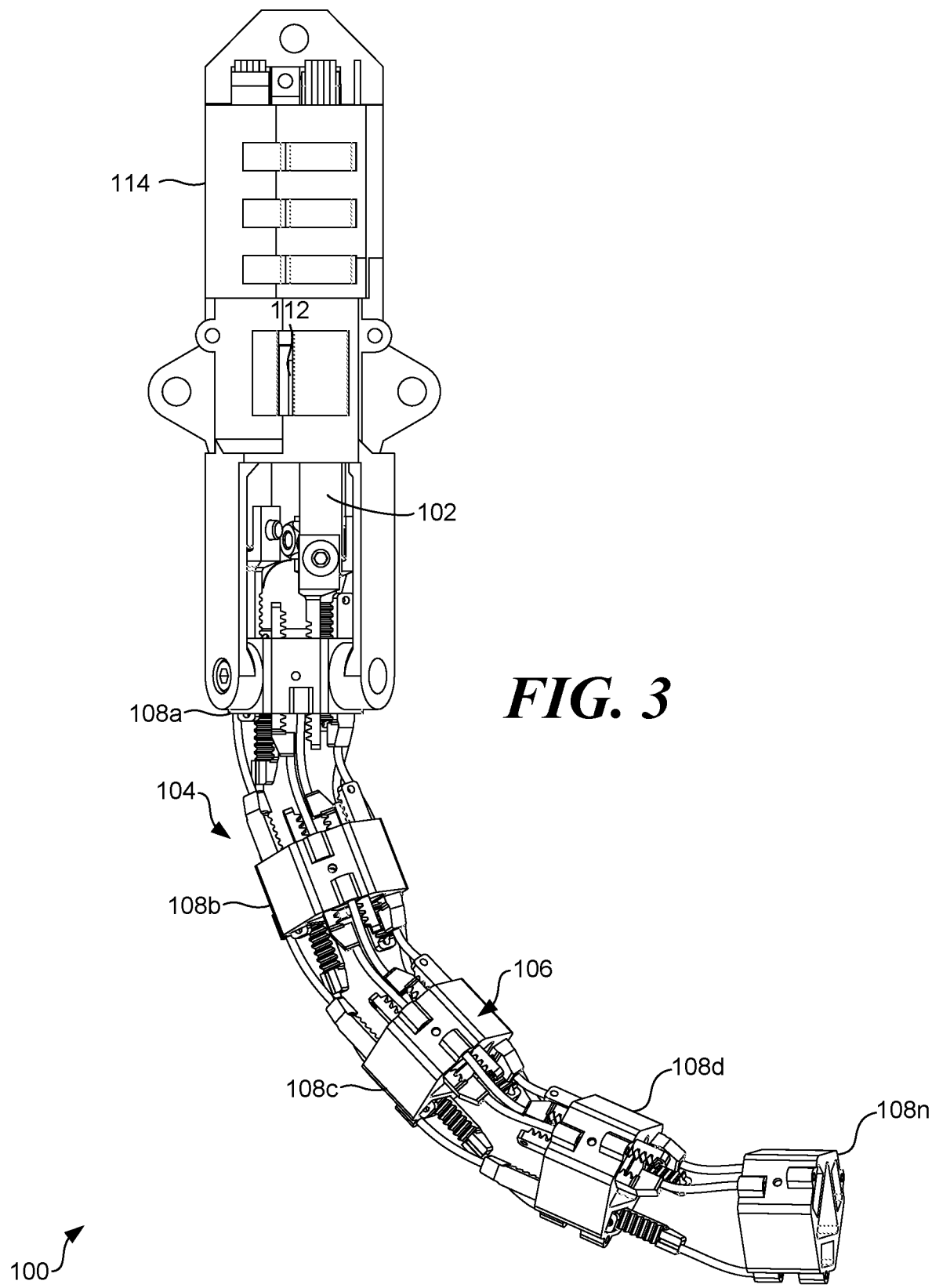
FIG. 3 is a bottom view of the robotic system having the extensible continuum manipulator according to various embodiments of the present disclosure.
Figure 4:
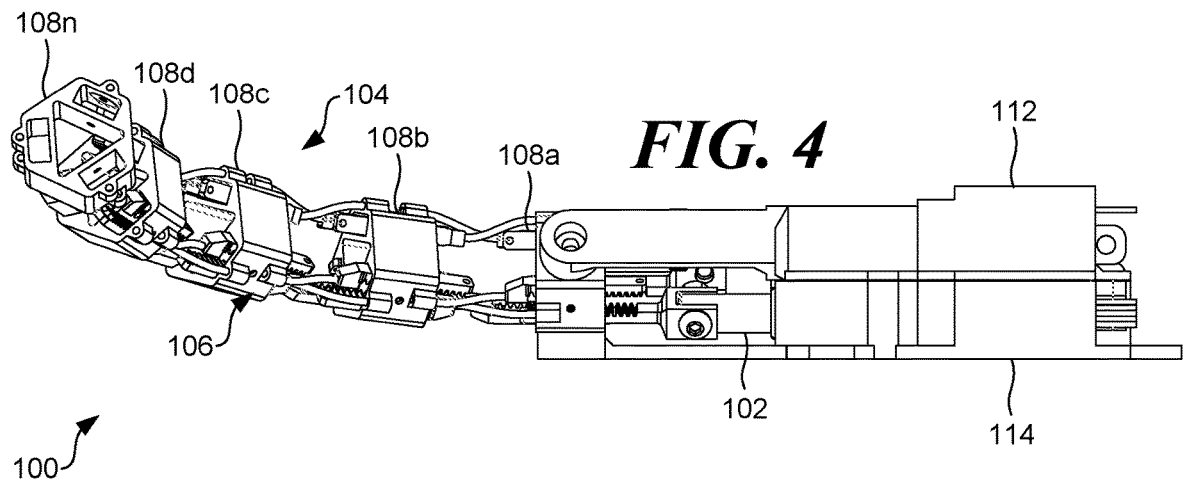
FIG. 4 is a side perspective view of the robotic system having the extensible continuum manipulator according to various embodiments of the present disclosure.
Figure 5:
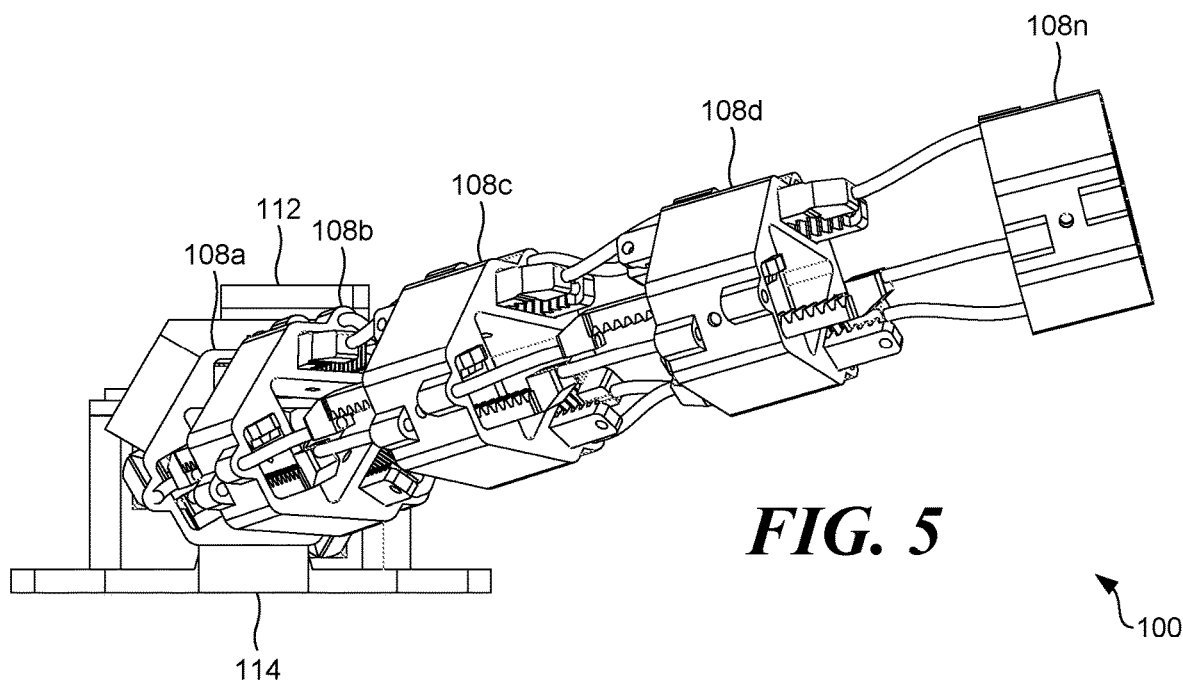
FIG. 5 is a front perspective view of the robotic system having the extensible continuum manipulator according to various embodiments of the present disclosure.

The continuum manipulator 104 may include an extensible continuum manipulator (ECM) body 106. The extensible continuum manipulator body 106 may include, for example, a multitude of subsegments 108a ... 108n (collectively "subsegments 108") serially connected to one another, thereby forming an elongated extensible continuum manipulator body 106 that projects laterally from a base of the continuum manipulator 104. In some examples, a number of the subsegments 108 may be two to ten, or other suitable number; however, the disclosure is not limited to these numbers of subsegments 108. FIG. 1, for example, illustrates five subsegments 108. The one or more actuators 102 may include a multitude of linear actuators, such as three to six; however, the disclosure is not limited to these numbers of actuators 102. FIG. 1, for example, illustrates three linear actuators.

Subsegments 108 that are proximal to the actuator 102 may be referred to as proximal subsegments 108 and subsegments 108 that are further away from the actuator 102 may be referred to as distal subsegments 108. For instance, a most proximal one of the subsegments 108a may be coupled to the one or more actuators 102 using a coupling rack 110, and a most distal one of the subsegments 108n may be coupled to an end effector (not shown). The one or more actuators 102 may be encased in a housing using a top cover 112 and a bottom cover 114, which may be used to mount the robotic system 100 to a suitable base. A base of the robotic system 100 may be fixed to a table, workbench, or other suitable area. The robotic system 100 may further include a controller (not shown) comprising processing circuitry configured to control motion of the extensible continuum manipulator body in at least a three degrees-of-freedom (3DoF) manner, as will be discussed. In some embodiments, the controller includes a computing device, such as a device having at least one hardware processor, memory, a data bus, and program instructions stored in the memory and executable by at least one hardware processor to control operation of the continuum manipulator 104.

Figure 11:
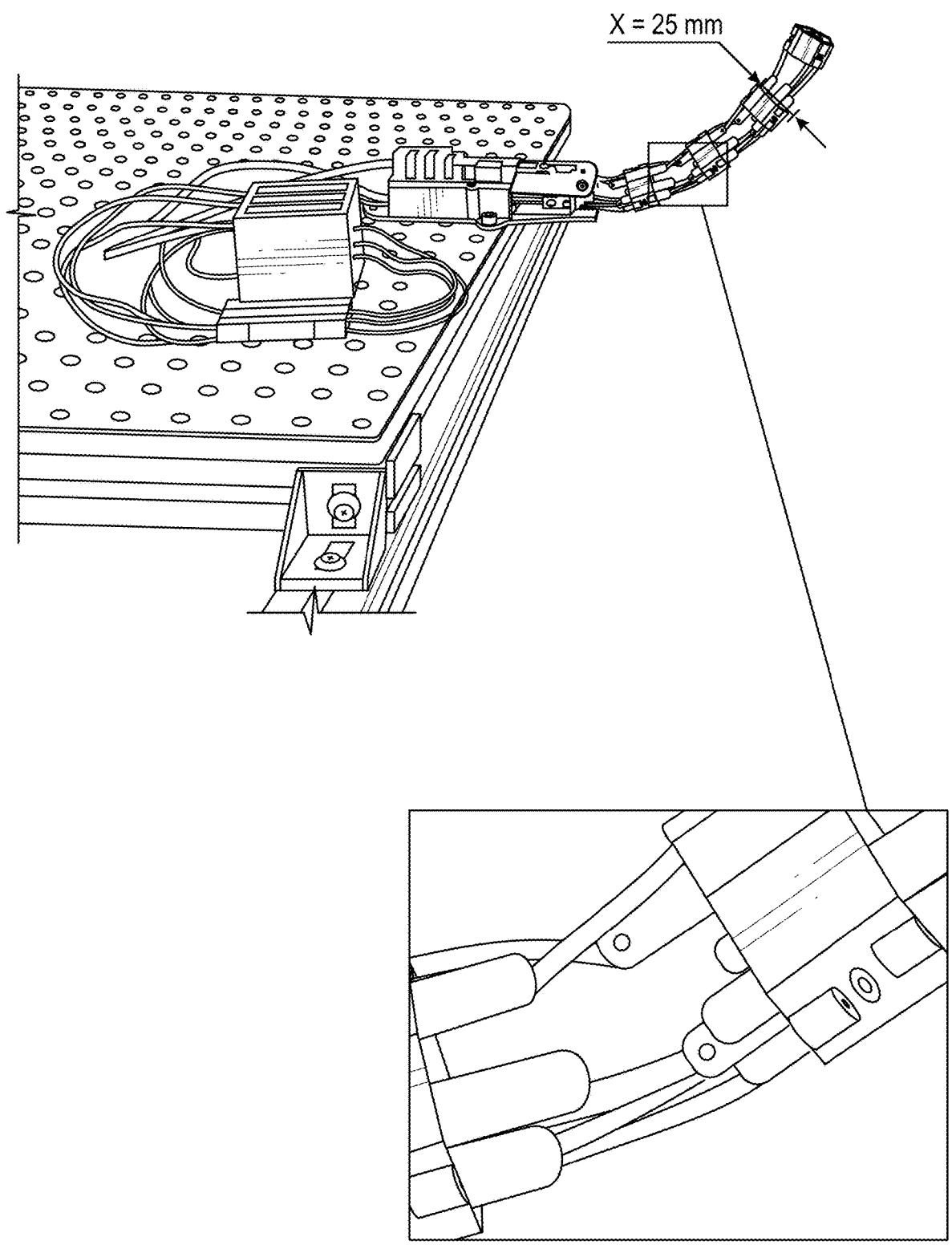
FIG. 11 is a photograph depicting a perspective view of the robotic system having the extensible continuum manipulator according to various embodiments of the present disclosure.

In some embodiments, a rigid coupling hybrid mechanism (RCHM) may be employed to take advantage of traditional hybrid mechanism structures, but uses specific transmission mechanisms to couple adjacent subsegments 108. According to the embodiments described herein, curvature bending robots based on rigid links become possible and, more importantly, general manipulation robots with special mobility requirements are possible. In some embodiments, the continuum manipulator 104 achieves three DoF, in which two achieve the spatial bending mobility and one achieves extension mobility along axis $a_1$. An overview of a prototype in accordance with the embodiments described herein is shown in FIG. 11.

With respect to the rigid coupling hybrid mechanism described above, the mechanism addresses challenges of designing spatial curvature bending mechanisms based on rigid links. Motion from the i-th subsegment 108 drives the (i+1)-th subsegment 108 instead of transmitting motion directly from a base to each subsegment 108. The transmission of motion transmission is realized by the rigid coupling hybrid mechanism that couples the (i+1)-th subsegment 108 with the i-th subsegment 108. As for basic mobility for each subsegment 108, traditional parallel mechanisms may be employed. Therefore, combining two mechanism components, a hybrid mechanism as described herein is able to amplify mobility of the subsegment 108 to manipulator scale. For instance, a three DoF spatial RCHM may be employed by serially connecting three DoF parallel mechanisms and using rigid transmission mechanisms to couple the adjacent parallel mechanisms.

Figure 6:
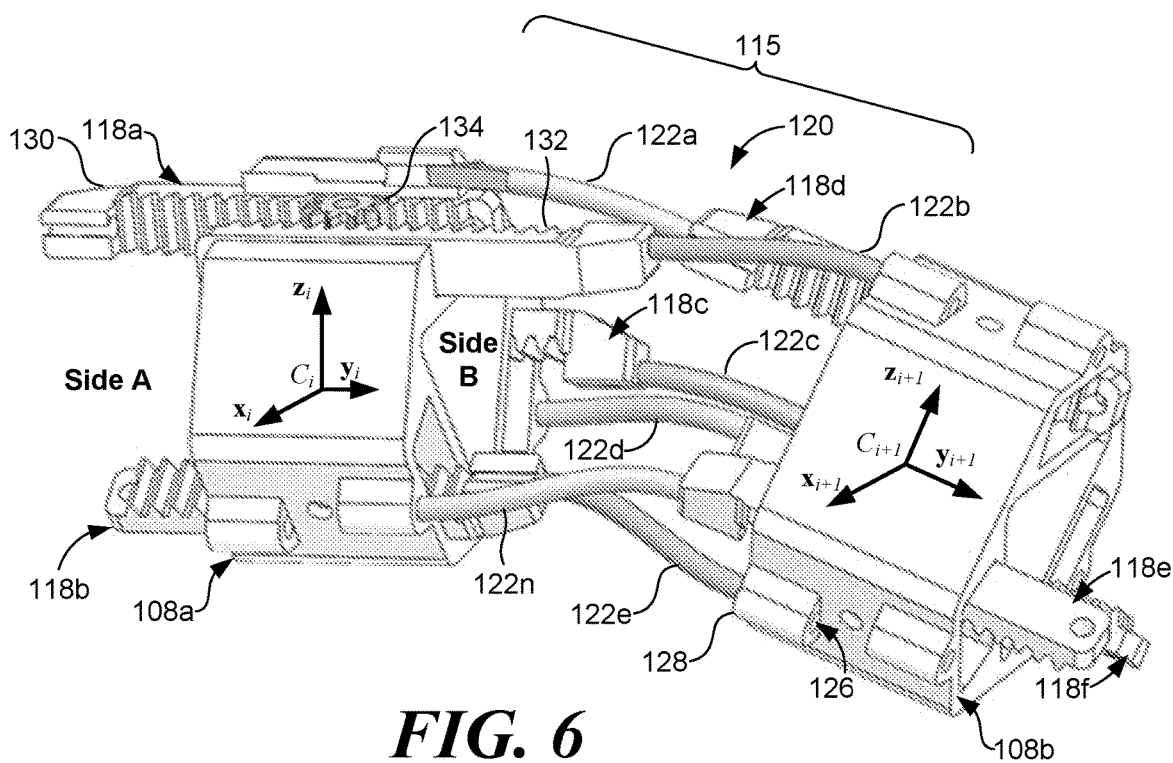
FIG. 6 is an enlarged view of adjacent subsegments of the extensible continuum manipulator according to various embodiments of the present disclosure.
Figure 7:
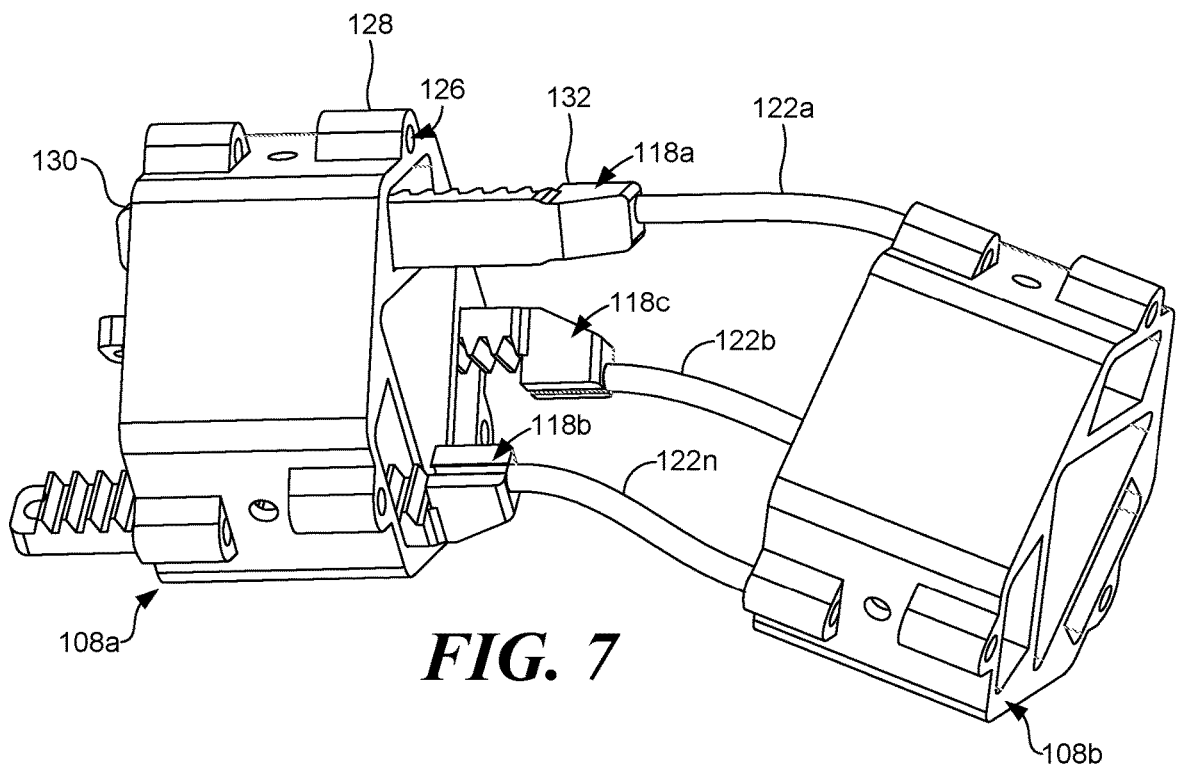
FIG. 7 is an enlarged view of a distal subsegment of the extensible continuum manipulator according to various embodiments of the present disclosure.

Referring now to FIGS. 6 and 7, enlarged views of two adjacent subsegments 108a, 108b (collectively "adjacent subsegments 108") of the extensible continuum manipulator body 106 are shown according to various embodiments. The adjacent subsegments 108 may be coupled to one another using a coupling arrangement 115 such that, when moved by the one or more actuators 102, a most proximal one of the subsegments 108a (e.g., a subsegment 108 coupled to an actuator 102) propagates subsegment motion to distal ones of the subsegments 108b ... 108n. For instance, the coupling arrangement 115 causes a most proximal one of the subsegments 108a, when driven using the one or more actuators 102, to induce movement of a second one of the subsegments 108b, which induces movement of a third one of the subsegments 108c, and so forth According to various embodiments, the coupling arrangement 115 may include a multitude of rack-and-pinion transmission sets 118 coupling the adjacent ones of the subsegments 108. Referring to the adjacent subsegments 108 shown in FIG. 6, the adjacent subsegments 108 may include a first subsegment 108a and a second subsegment 108b that are coupled to one another by a multi-chain parallel mechanism 120. The multi-chain parallel mechanism 120 may include a multitude of rods 122a ... 122n (collectively "rods 122") as well as other components, as will be described. In some embodiments, all or a portion of the rods 122 are rigid with joints; however, in alternative embodiments, all or a portion of the rods 122 are flexible, as will be described. A number of the rods 122 may be three to eight; however, the disclosure is not limited to these numbers of rods 122 and other suitable number of rods 122 may be employed. FIG. 6, for example, depicts six of the rods 122.

The first subsegment 108a may include first rack-and-pinion sets 118a ... 118c coupled to proximal ends of a first portion of the rods 122 (e.g., rods 122b, 122c, 122e). Distal ends of the first portion of the rods 122 may be coupled to a body of the second subsegment 108b. For instance, the distal ends of the first portion of the rods 122 may be positioned in an aperture 126 on a curved projection 128 located on an exterior of a housing of the second subsegment 108b; however, other suitable portions of the second subsegment 108b may be employed.

The second subsegment 108b may include second plurality of rack-and-pinion sets 118d ... 118f coupled to distal ends of a second portion of the rods 122 (e.g., rods 122a, 122d, 122n). Proximal ends of the second portion of the rods 122 may be coupled to a body of the first subsegment 108a. For instance, similar to the distal ends of the first portion of rods 122, the proximal ends of the second portion of the rods 122 may be positioned in an aperture 126 on a curved projection 128 located on an exterior of a housing of the first subsegment 108a; however, other suitable portions of the first subsegment 108a may be employed.

Referring now to a representative one of the rack-and-pinion sets 118, individual ones of the rack-and-pinion sets 118 may include a first rack 130, a second rack 132, and a pinion 134 positioned, for instance, between the first rack 130 and the second rack 132. For instance, the first rack 130 may include teeth facing the second rack 132 and the second rack 132 may include teeth facing the first rack 130. The pinion 134 may resemble a gear having projections that movably couple to the teeth of the first rack 130 and the second rack 132. Due to the position of the pinion 134, a lateral pulling motion applied to the first rack 130 causes the first rack 130 to displace relative to the second rack 132.

In some embodiments, if the first subsegment 108 is a first one of the subsegments 108 in a chain of subsegments 108, the first subsegment 108 may include multiple rack-and-pinion sets 118a . . . 118c, each comprising a first rack 130 coupled to a respective one of the plurality of linear actuators 102, a second rack 132 coupled to a body of the proximal one of the plurality of subsegments 108b, and a pinion 134 rotatably coupled to and positioned between the first rack 130 and the second rack 132. The rack-and-pinion sets 118 may be coupled to the actuators 102 such that lateral force provided by the actuators 102 causes the first rack 130 to shift relative to the second rack 132 through rotation of the pinion 134.

Accordingly, the first rack-and-pinion set 118a may have a rack coupled to a proximal end of the rod 122b, the second rack-and-pinion set 118b may have a rack coupled to a proximal end of the rod 122e, and a third rack-and-pinion set 118c having a rack coupled to a proximal end of the rod 122c. A distal end of the rods 122b, 122e, and 122c may be coupled to the body of the second subsegment 108b.

Similarly, the fourth rack-and-pinion set 118d comprises a rack coupled to a distal end of the rod 122a, a second rack-and-pinion set 118e having a rack coupled to a distal end of the rod 122d, and a third rack-and-pinion set 118f having a rack coupled to a distal end of the rod 122n. A proximal end of the rods 122a, 122d, and 122n may be coupled to the body of the first subsegment 108a, as shown in FIG. 6. Further, in some embodiments, the rods 122b, 122c, and 122e, may be referred to as "driving rods" that are configured to induce motion in the second subsegment 108b, whereas the rods 122a, 122d, and 122n may be referred to as "measuring rods" that are configured to measure motion generated by the first subsegment 108a.

As noted above, in some embodiments, individual ones of the rods 122 may be flexible. As such, the coupling arrangement 115 may be configured to provide at least two decoupled and independent rotations with respect to perpendicular axes and at least one independent axial extension. In some embodiments, the rods 122 are rigid and comprise at least one joint. In some embodiments, the at least one joint is selected from a group consisting of a prismatic joint, a revolute joint, and a spherical joint.

FIG. 9 shows the topological structure of the RCHM, which includes a base, actuation, a link, a parallel mechanism (PM), and a rigid transmission mechanism (RTM). The PMs realize basic motion for each subsegment 108. The RTMs serve as rigid coupling mechanisms that transmit motion from the i-th PM to the (i+1)-th PM. Therefore, the overall motion sequence is that the actuators drive PM1 directly, then RTM1 copies the PM1 motion to drive PM2. After PM2 moves, RTM2 transmits the motion from M2 to drive PM3, and so forth.

RCHM has various advantages as compared to traditional cable driven hyper-redundant designs. First, RCHM usually has good rigidity due to the parallel mechanism used for each subsegment 108, which is known to have higher stiffness, precision, and load bearing in comparison to its serial counterpart. Moreover, using rigid transmission design avoids the commonly observed cable driven issues, such as the unidirectional driving problem and the cable tension control problem. These two features, together, provide the RCHM with desirable rigidity and enable the mechanism to respond to high frequency input, which is critical for applications that need high speed or high dynamic motion. Further, since the RCHM has centralized actuation, the weight of the robot itself could be significantly reduced. As a result, the motion accuracy of the robot could be increased, and the controller could be simplified.

Figure 10:
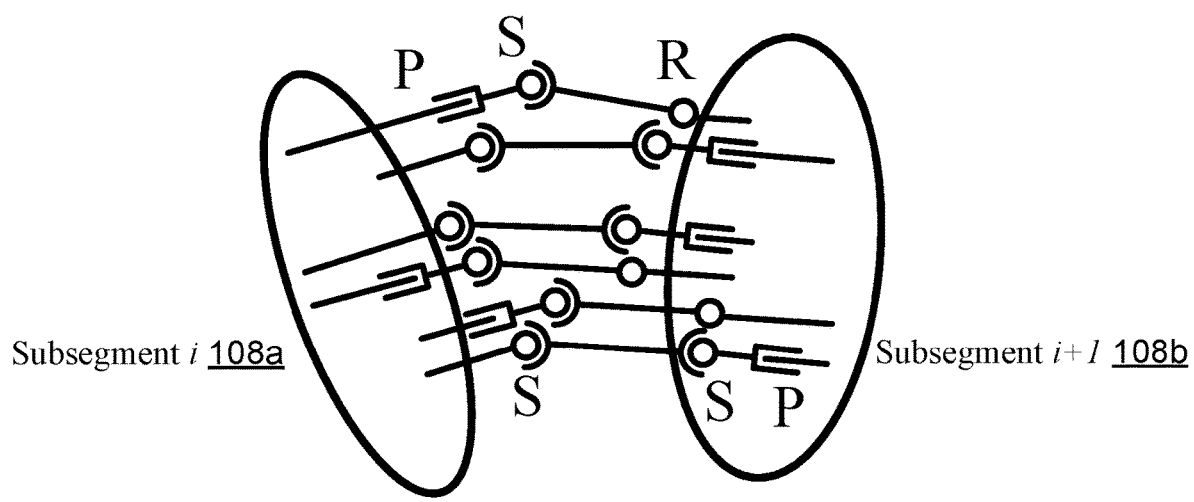

Referring now to FIG. 10, adjacent subsegments 108a, 108b are shown where a parallel mechanism includes a prismatic joint P, a revolute joint R, and a spherical joint S, which is also referred to as a ball joint. An actuated joint is labeled by an underlined letter. In RCHM design, it is beneficial is to select an appropriate parallel mechanism to realize the subsegment motion, which may include 2R1T (two radial rotations and one axial translation) motion in various embodiments. However, to take advantage of motion generated by a 3PSR mechanism and transmit motion to a next subsegment 108, another three chains (e.g., rods 122) are required. These three additional chains (e.g., rods 122) may be placed close to the three original chains respectively so that each additional chain behaves simultaneously and similarly with its original chain counterpart. This way, the additional chains are able to "measure" the motion generated by the original chains.

Therefore, these three additional chains may be referred to as measuring PMs while the original three chains may be referred to as measuring PMs due to their different functions. Notably, due to the physical thickness of the subsegments 108, the closeness of the additional rods 122 with the original rods 122 would never become zero, which leads to the fact that the measuring PM could never exactly copy the motion of the driving PM. As a result, non-uniform twist motions (the non-uniformity could be very small if the two chains were designed close enough) among subsegments 108 may occur.

Figure 8:
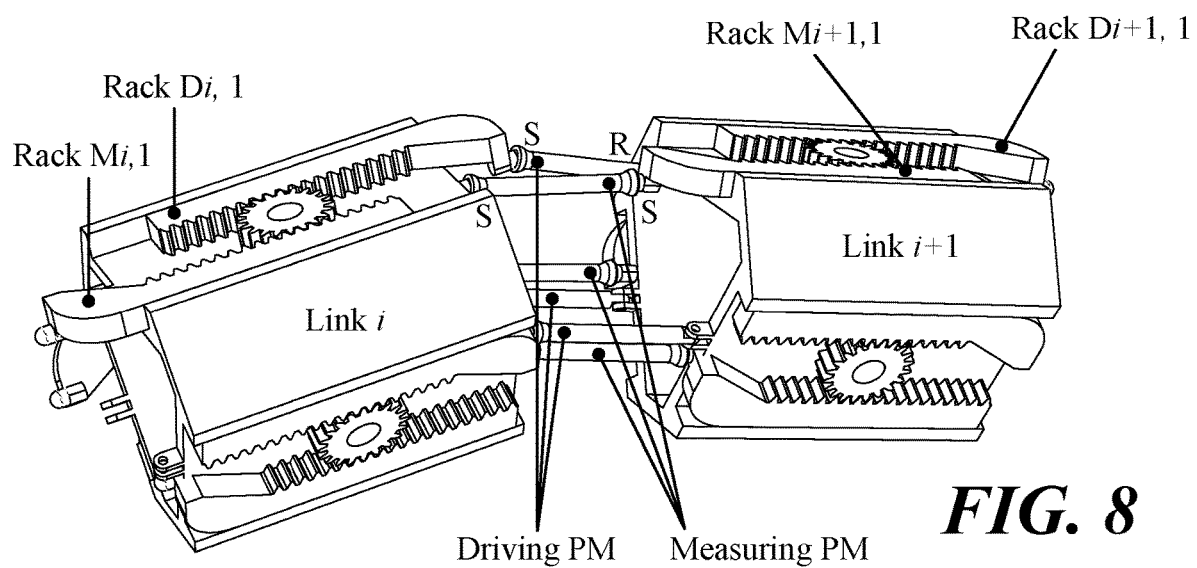
FIG. 8 is an enlarged view of adjacent subsegments of the extensible continuum manipulator and rack-and-pinion sets thereof according to various embodiments of the present disclosure.

Since the driving PM is already fully constrained, the three additional rods 122 cannot exert more constraints onto the robotic system 100. Therefore, in some embodiments, three SSP rods 122 may be employed to guarantee enough degrees of freedom for the measuring PM. FIG. 8 shows one potential subsegment design based on this mechanism configuration and FIG. 10 is the corresponding kinematic diagram. The overall mobility can be verified by the Grübler-Kutzbach criterion (G-K criterion) as:

$$M = 6n - \sum_{i=1}^{j}(6 - f_i) \quad \text{(eq. 1)}$$
$$= 6 \times 13 - 3 \times (5 + 3 + 5) - 3 \times (3 + 3 + 5) = 6$$

where n is the number of moving bodies, j is the number of joints, and $f_i$ is the corresponding DoF of joint i. Although the calculation shows the mechanism having six degrees-of-freedom, three of them are actually internal DoF (self-rotation with respect to the axis connecting the two ball joint centers) induced by the SS chains, which do not affect the overall mobility. Therefore, the actual mobility of the 3PSR-3SSP mechanism may be three.

The PM and rack-and-pinion transmission form a motion propagation mechanism. For instance, referring to FIG. 8, if an input motion (indicated by the solid arrow) is exerted on rack Mi,1, rack Di,1 is pushed right through the pinion 134. This motion causes the clockwise rotation of link i+1, which further induces the relative motion of rack Mi+1,1 (indicated by the dashed arrow). Because of the gear, this relative motion continues to be transmitted onto rack Di+1,1, which becomes the driving motion for the next subsegment 108.

Using rigid links and joints larger loads may be employed and higher stiffness may be achieved. However, rigid links can complicate the mechanical structure of the robotic system 100 such that a manufacturing process is more challenging in terms of manufacturing tolerance control problems (e.g., backlash is rapidly amplified due to the motion propagation characteristics of this type of mechanism). Therefore, in some embodiments, flexible parallel mechanisms (FPM) are described that in place of a rigid link-based PM. The flexible structure facilitates the manufacturing process significantly and increases accuracy by avoiding backlash (e.g., the deformation of the material itself does not induce backlash). Moreover, the flexible structure has the same compliant-to-obstacle benefit as traditional continuum robots.

Referring again to FIG. 6, the subsegments 108 use flexible rods 122 in lieu of rigid links and joints. Similarly, the six chain FPM is subdivided to one driving PM and one measuring FPM. After changing to flexible rods 122, mounting and connection among parts becomes easier. For instance, the rods 122 are easily connected with the racks 130, 132 and the subsegments 108 using glue or another suitable adhesive. The rack-and-pinion sets 118 may also be placed internally to achieve better assembly accuracy.

Referring back to FIG. 1, the overall design of the robotic system 100 with the continuum manipulator 104 is shown, where the extensible continuum manipulator body 106 includes six serially connected subsegments 108 (or other suitable number of subsegments 108). A customized housing that includes a top cover 112 and a bottom cover 114 is configured to retain and mount three linear actuators 102. A connection between the actuation module and the extensible continuum manipulator body 106 is achieved by a specifically designed first link and three special racks.

For the preliminary kinematic analysis, certain assumptions may be made to simplify computations and, accordingly, speed up operating of a computing device while utilizing less memory. Due to similar mobility as traditional extensible continuum manipulators, circular arc bending may be assumed. That is, each subsegment 108 may be treated as having a constant curvature bending continuum robot section and each rod 122 together with its rack 130, 132 may be regarded as a driving rod 122 for that continuum robot section. To this end, each shape of the subsegment 108 may be fully defined by the three chains in the driving FPM, and the three chains in the measuring FPM measure corresponding arc length and transmits to the next subsegment 108.

Figure 12:
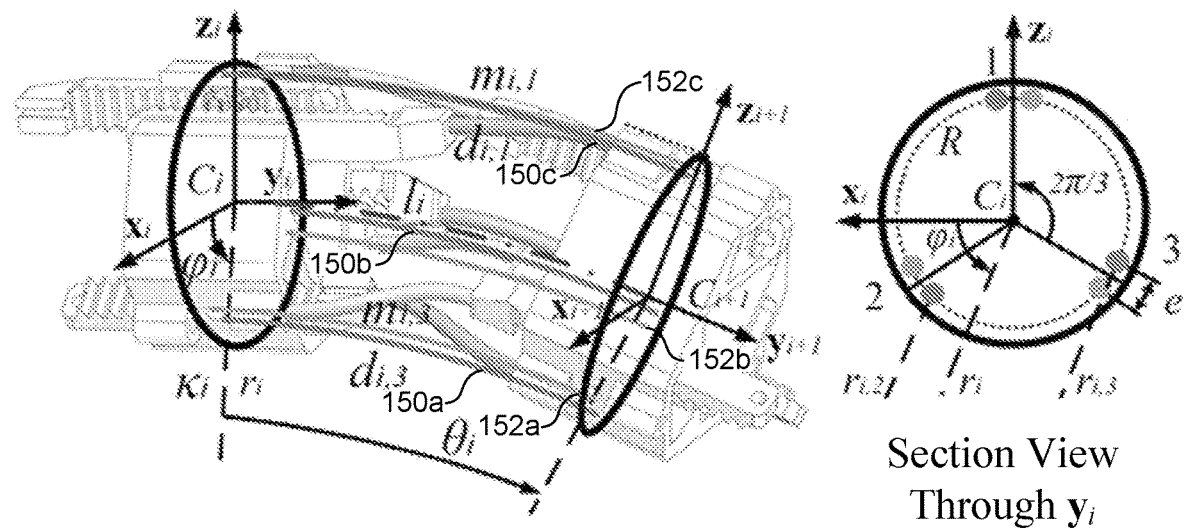
FIG. 12 is kinematic model based on a circular arc bending assumption according to various embodiments of the present disclosure.

FIG. 12 illustrates a subsegment kinematic model based on the circular arc bending assumption, where arcs 150a . . . 150c are an abstraction of the driving chains with length $d_{i,j}$ and the arcs 152a . . . 152c are an abstraction of the measuring chains with length $m_{i,j}$. $i \in \{1,2,3,4\}$ represents the i-th link and $j \in \{1,2,3\}$ represents the j-th chain in one subsegment 108. A body fixed frame $\Sigma C_i = (C_i, x_i, y_i, z_i)$ is placed at the center of the i-th link. Variables $l_i$, $k_i$, $r_i$, and $\theta_i$ denote the arc length, curvature, radius, and central angle for the central bending arc (in a dash-dot line), respectively. Variable $\Phi_i$ is the angle of the bending plane from $x_i$ axis, and R is the distance of the driving/measuring arcs from the central arc. Based on mathematical definitions, the following relationships are self-satisfied:

$$l_i = \theta_i r_i \qquad \text{(eq. 2)},$$

$$r_i = 1/k_i \qquad \text{(eq. 3)}.$$

Therefore, with three arc lengths $d_{i,j}$, the bending shape is fully determined. The forward kinematics may be obtained via:

$$l_i = \frac{d_{i,1} + d_{i,2} + d_{i,3}}{3}, \qquad \text{(eq. 4)}$$

$$k_i = \frac{2\sqrt{d_{i,1}^2 + d_{i,2}^2 + d_{i,3}^2 - d_{i,1}d_{i,2} - d_{i,1}d_{i,3} - d_{i,2}d_{i,3}}}{R(d_{i,1} + d_{i,2} + d_{i,3})}, \qquad \text{(eq. 5)}$$

$$\varphi_i = -\mathrm{atan2}(d_{i,3} + d_{i,2} - 2d_{i,1}, \sqrt{3}(d_{i,3} - d_{i,2})) + \frac{e}{2R}, \qquad \text{(eq. 6)}$$

where the second term in eq. 6 is the angle shift due to the mounting point offset of the driving arc on the sectional view plane (the red dots are not exactly located on the $z_i$ axis).

Knowing the bending shape, the three measuring arc lengths could be obtained by inverse kinematics, such as:

$$m_{i,j} = l_i - l_i k_i R \cos\left(\varphi_i + \frac{e}{2R} + \frac{7\pi}{6} - \frac{2\pi}{3}j\right). \qquad \text{(eq. 7)}$$

For the (i+1)-th subsegment, the driving arc length should be replaced by the measuring arc length from the i-th subsegment, that is:

$$d_{i+1,j} = m_{i,j} \qquad \text{(eq. 8)}.$$

Note that the above and the following equations do not include the $k_i = 0$ case, which could be easily handled in actual programming by manually assigning values to all the variables.

The overall kinematic model may be obtained as long as the subsegment wise kinematics is known. That is, with $l_i$, $k_i$, and $\varphi_i$ known, the vector from $C_i$ to $C_{i+1}$ is obtained as:

$$p_{i,i+1} = r_i \sin\theta_i y_i + (r_i - \cos\theta_i r_i)(\cos\varphi_i x_i - \sin\varphi_i z_i) \qquad \text{(eq. 9)}.$$

The rotation from $\Sigma C_i$ to $\Sigma C_{i+1}$ may be formulated as:

$$^i R_{i+1} = e^{\theta_i \hat{\xi}} \qquad \text{(eq. 10)}$$

where $\xi = -\sin\varphi_i x_i - \cos\varphi_i z_i$ is the rotation axis vector and the hat above $\xi$ indicates the skew-symmetric expansion. Eq. 10 may be evaluated by the Rodrigues' Formula as:

$$^i R_{i+1} = I + \sin\theta_i \hat{\xi} + \hat{\xi}^2 (1 - \cos\theta_i) \qquad \text{(eq. 11)}$$

With local displacement $p_{i,i+1}$ and $^i R_{i+1}$ known, the global displacement of $\Sigma C_i$ can be obtained recursively with the initial displacement of $p_1 = 0$ and $R_1 = I$:

$$p_i = p_{i-1} + p_{i-1,i} \qquad \text{(eq. 12)},$$

$$R_i = {^{i-1}R_i} R_{i-1} \qquad \text{(eq. 13)}.$$

The workspace of the extensible continuum manipulator 104 described herein is defined by all the points that the manipulator tip can reach in a three-dimensional space. Based on the measurement of prototype, R=25 mm, range of d is from 42 mm to 62 mm, and e=2.3 mm.

Figure 13:
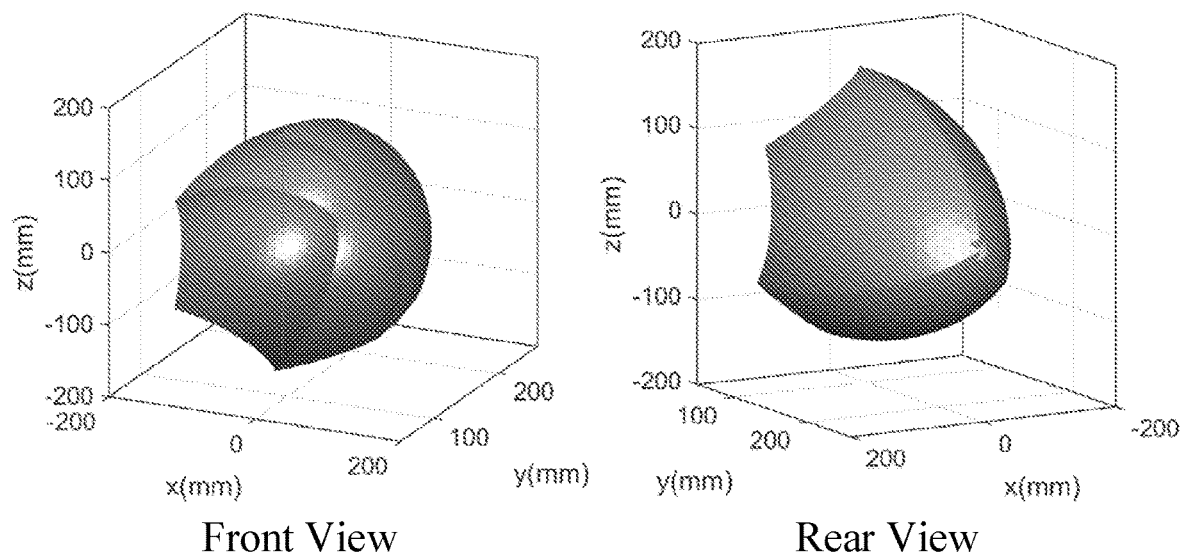
FIG. 13 is a graph illustrating a workspace of the robotic system having the extensible continuum manipulator according to various embodiments of the present disclosure.

The workspace of the extensible continuum manipulator 104 is generated accordingly and shown in FIG. 13. The workspace shows a fully shortened manipulator having a length, for example, of 176 mm and a fully extended case having a length of, for example, 256 mm, although other dimensions may be employed. The maximal extension ratio (for what percentage the ECM can extend the most) is (256−176)/176=45.45%. The three ridges appearing on both the concave and the convex surfaces correspond to a single actuator driving cases.

Further, due to the rod mounting angle shift e/R≠0, the measuring PM cannot exactly copy the driving PM motion. This leads to a twist motion along the manipulator axial direction, which breaks the desired uniform motion for each subsegment 108. To evaluate the non-uniformity induced by this phenomenon, different angle shift e/R values are tested and the corresponding manipulator configurations with the same inputs (e.g., $d_{1,1}$=42 mm, $d_{1,2}$=52 mm, $d_{1,3}$=52 mm) are plotted in FIG. 14, in which five more subsegments are added to make the twist motion more visible. Other colors indicate the four subsegments 108 in an example design.

Figure 14:
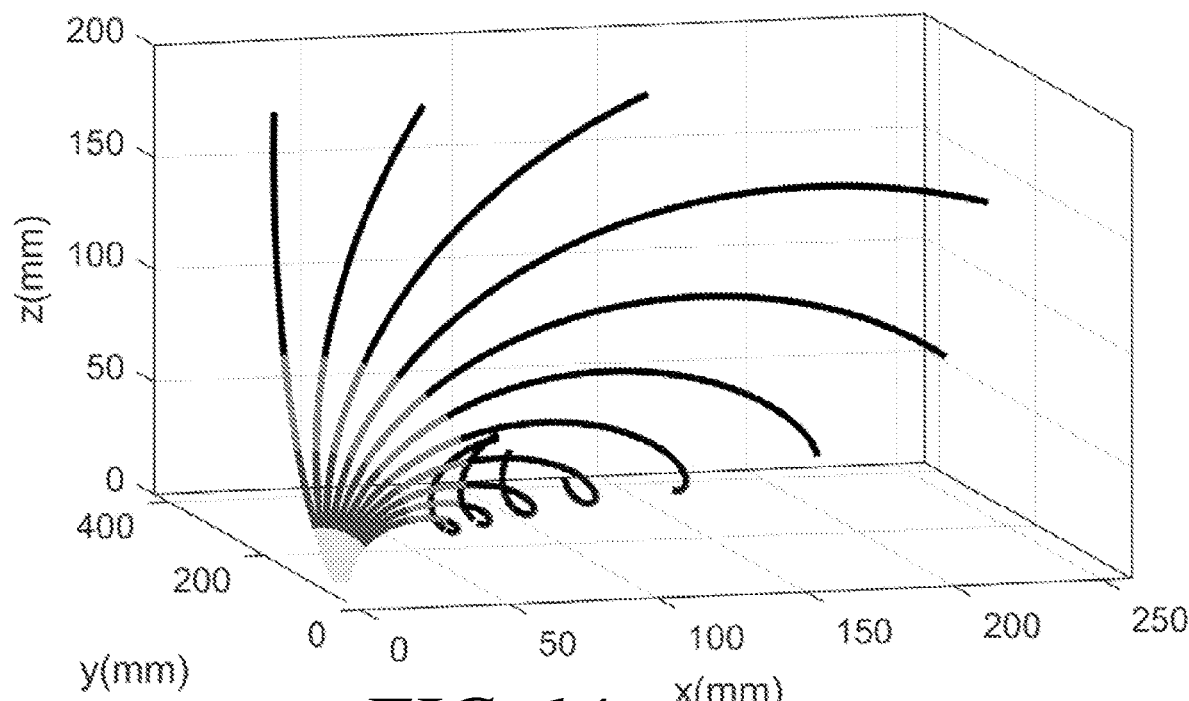
FIG. 14 is a graph illustrating a twist effect of the robotic system having the extensible continuum manipulator according to various embodiments of the present disclosure.

As shown in FIG. 14, the twist effect becomes quite serious as e/R is beyond ten degrees and more subsegments worsen the situation significantly. Therefore, for practical design purposes, reducing e to a value as small as possible and choosing fewer subsegments helps reducing the undesired twist motion. For the existing design with a minimized e value (e.g., 2.3 mm), the twist effect is also evaluated for different manipulator configurations.

Figure 15:
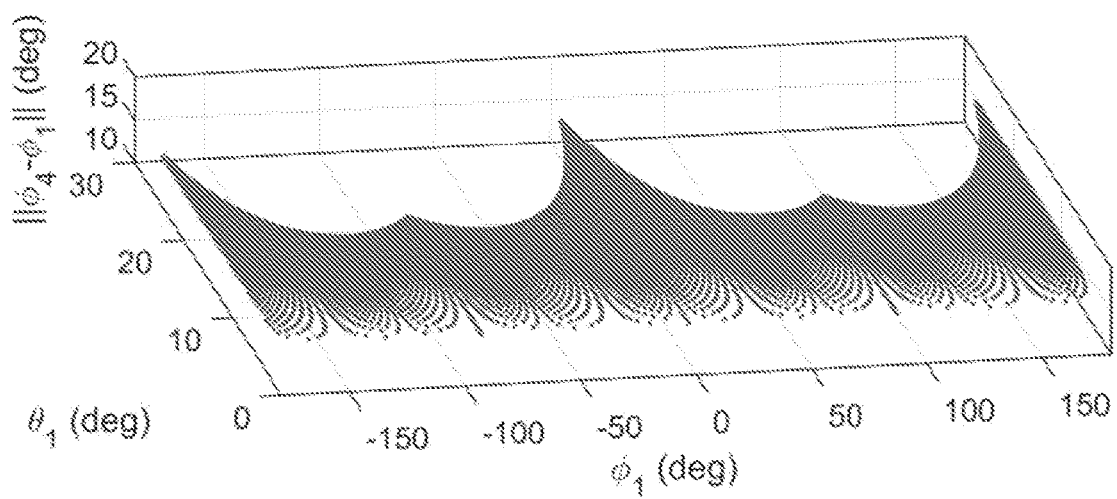
FIG. 15 is a graph illustrating a distribution of non-uniformity for different configurations of the robotic system having the extensible continuum manipulator according to various embodiments of the present disclosure.
Figure 16A:
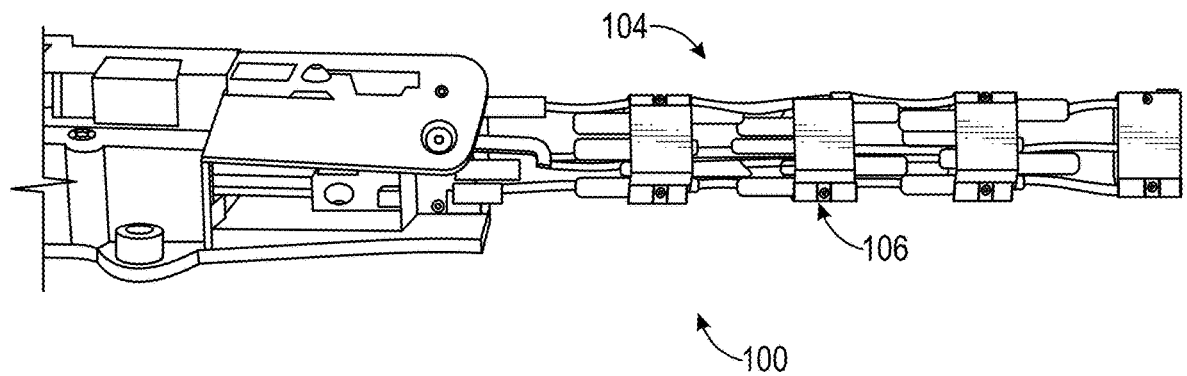
FIGS. 16A-16F are photographs depicting mobility of the robotic system having the extensible continuum manipulator according to various embodiments of the present disclosure.
Figure 16B:
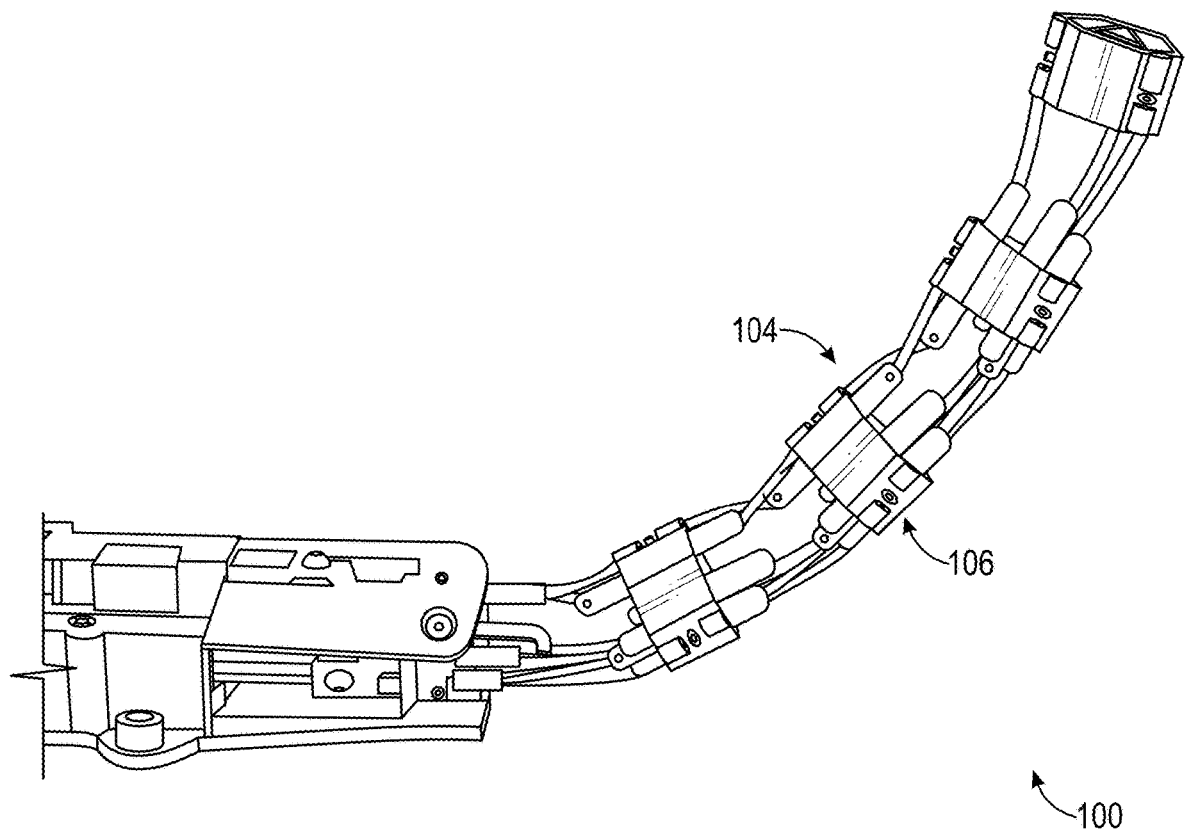
Figure 16C:
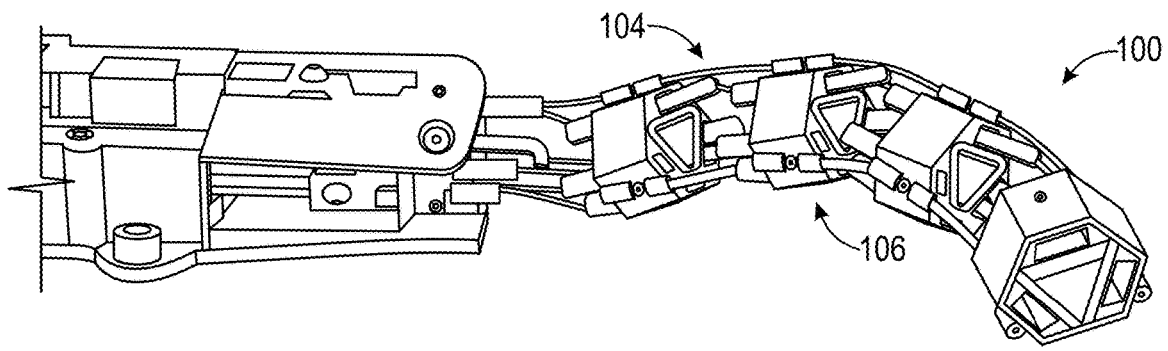
Figure 16D:
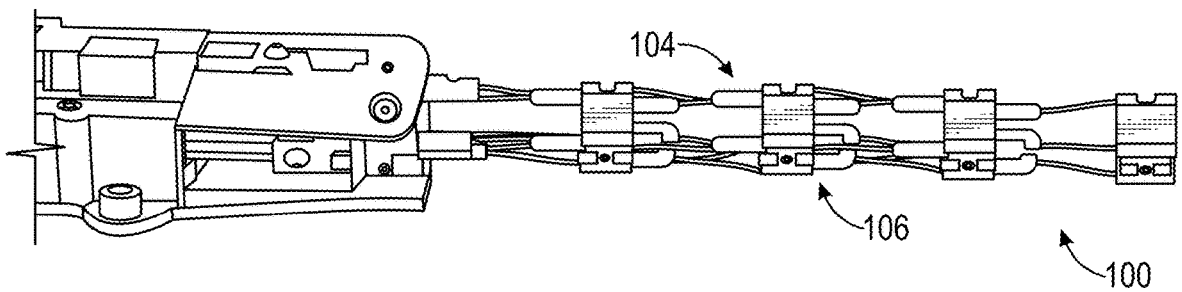
Figure 16E:
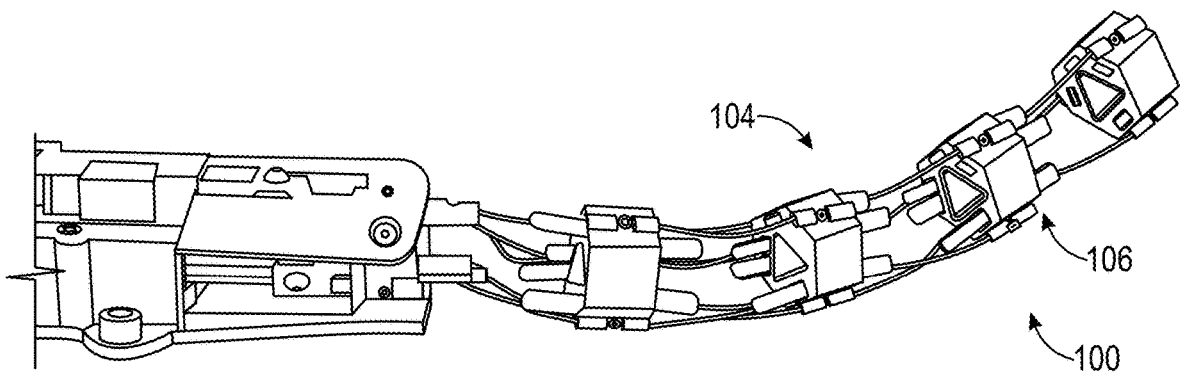
Figure 16F:
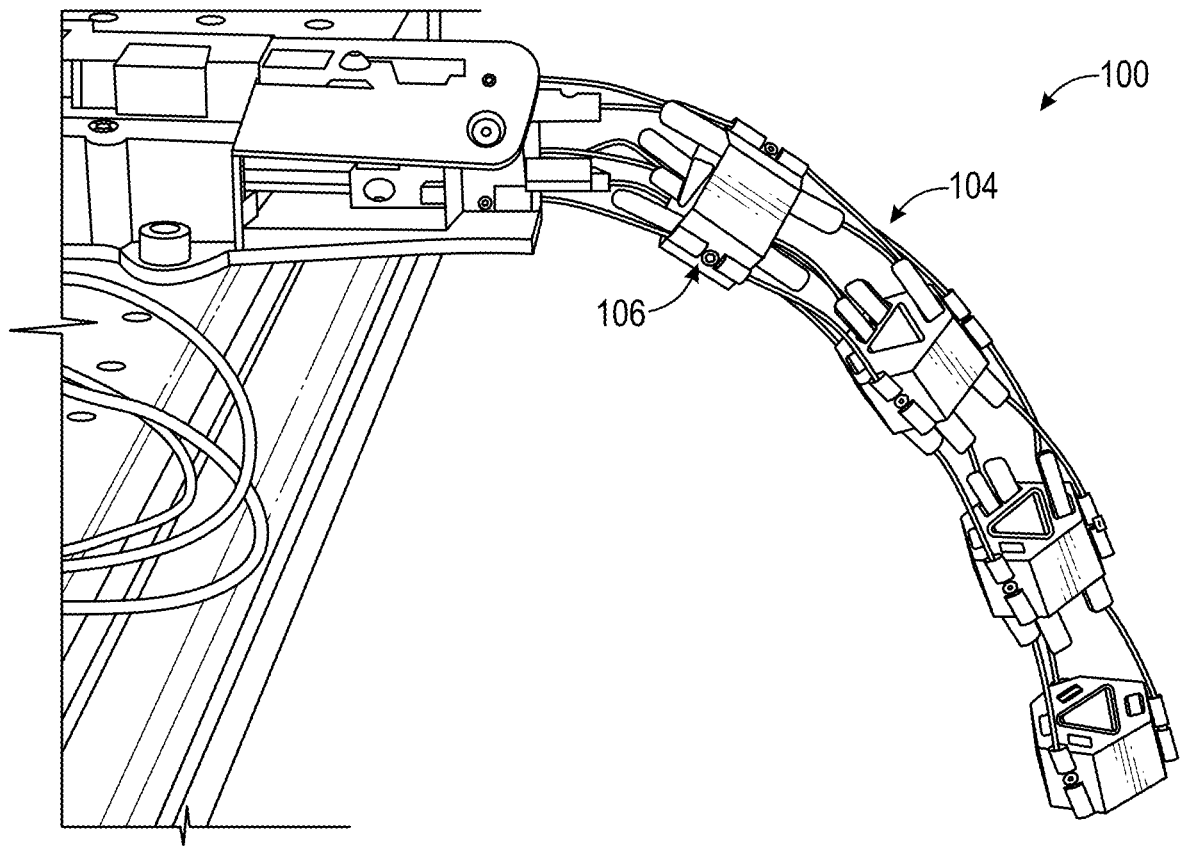

The non-uniformity is defined by the difference between the last subsegment bending plane angle $\varphi_4$ and the first subsegment bending plane angle $\varphi_1$. Numerical calculation is conducted and plotted in FIG. 15, which surprisingly shows that the non-uniformity (the value in the figure is 15.81°) is actually not affected by the manipulator configuration. This can be verified analytically by substituting eq. 8 into eq. 6, which yields:

$$-\tan\left(\varphi_{i+1} - \frac{e}{2R}\right) = \frac{m_{i,3} + m_{i,2} - 2m_{i,1}}{\sqrt{3}(m_{i,3} - m_{i,2})}, \quad \text{(eq. 14)}$$

Substituting Eq. (7) into Eq. (14) and evaluating, Eq. (14) is simplified as $$\varphi_{i+1} - \varphi_i = \frac{e}{R}, \quad \text{(eq. 15)}$$

which means that the twist effect only depends on the rod mounting angle shift e/R and the subsegment number.

To verify the proposed mobility of the new mechanism, a proof-of-concept prototype was integrated with 3D printing using, for example, ABS plastic as the building material. It is understood however, that the embodiments described herein are not limited to ABS plastic. In fact, other materials may be employed. As shown in FIGS. 16A-16F, three Actuonix linear actuators 102 (L12-30-210-6-P) with corresponding controller boards were used to drive the continuum manipulator 104 of the robotic system 100. For the rack-and-pinion transmission, 0.5 modulus nylon gears were utilized and customized racks were three-dimensionally printed. The flexible rods 122 were formed of fishing line with a 1.35 mm diameter. The rods 122 and plastic parts were connected using super glue.

As shown in FIGS. 16A-16F, the prototype exhibits the proposed 2R1T mobility, for which the most shortened length is measured as 177 mm and the most extended length as 234 mm. The extension ratio is computed as 32.2% which is smaller than the ratio predicted by the workspace analysis. This is partially due to the smaller range applied on the linear actuator to avoid potential damage on the prototype. The maximal bending angle was measured to be around 80 degrees.

Figure 17A:
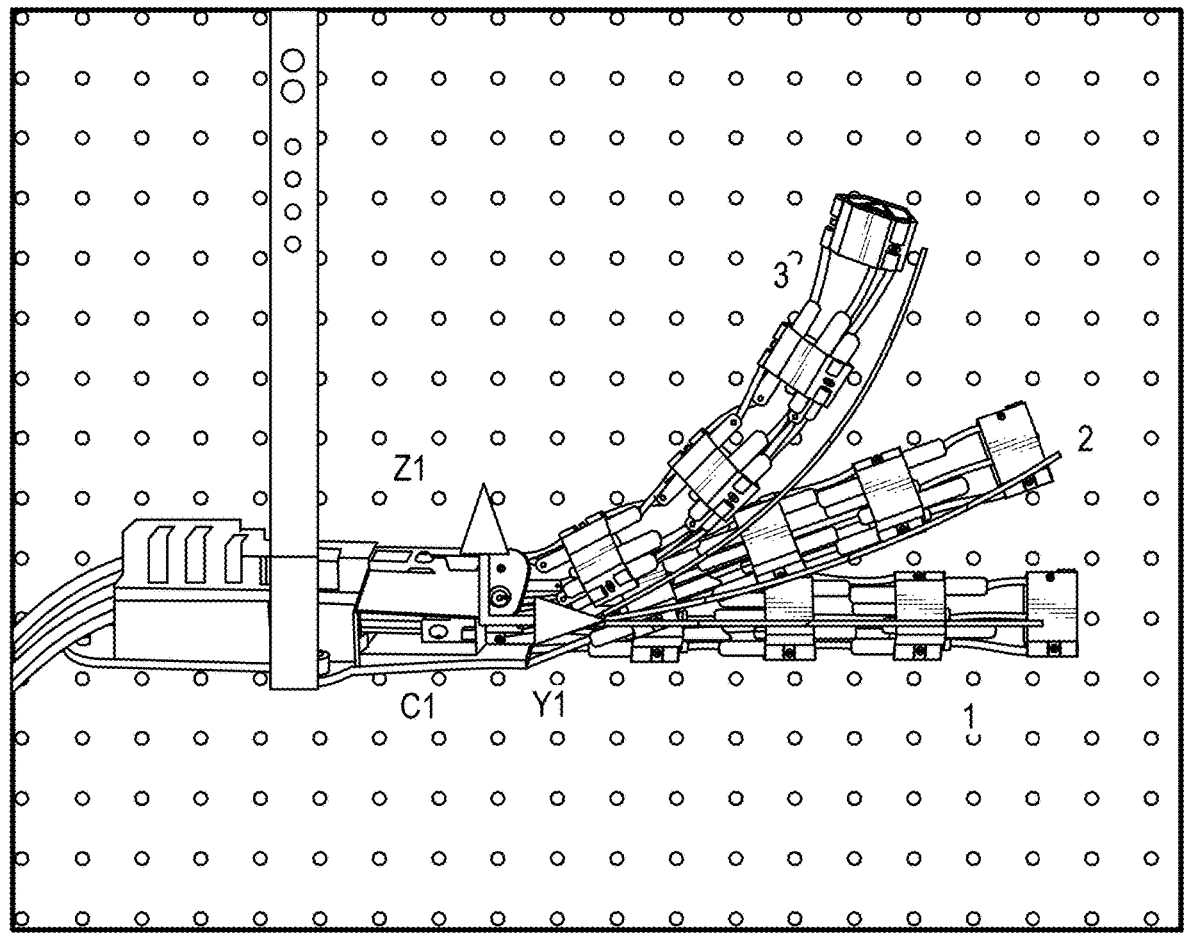
FIGS. 17A-17B are additional photographs depicting mobility of the robotic system having the extensible continuum manipulator according to various embodiments of the present disclosure.
Figure 17B:
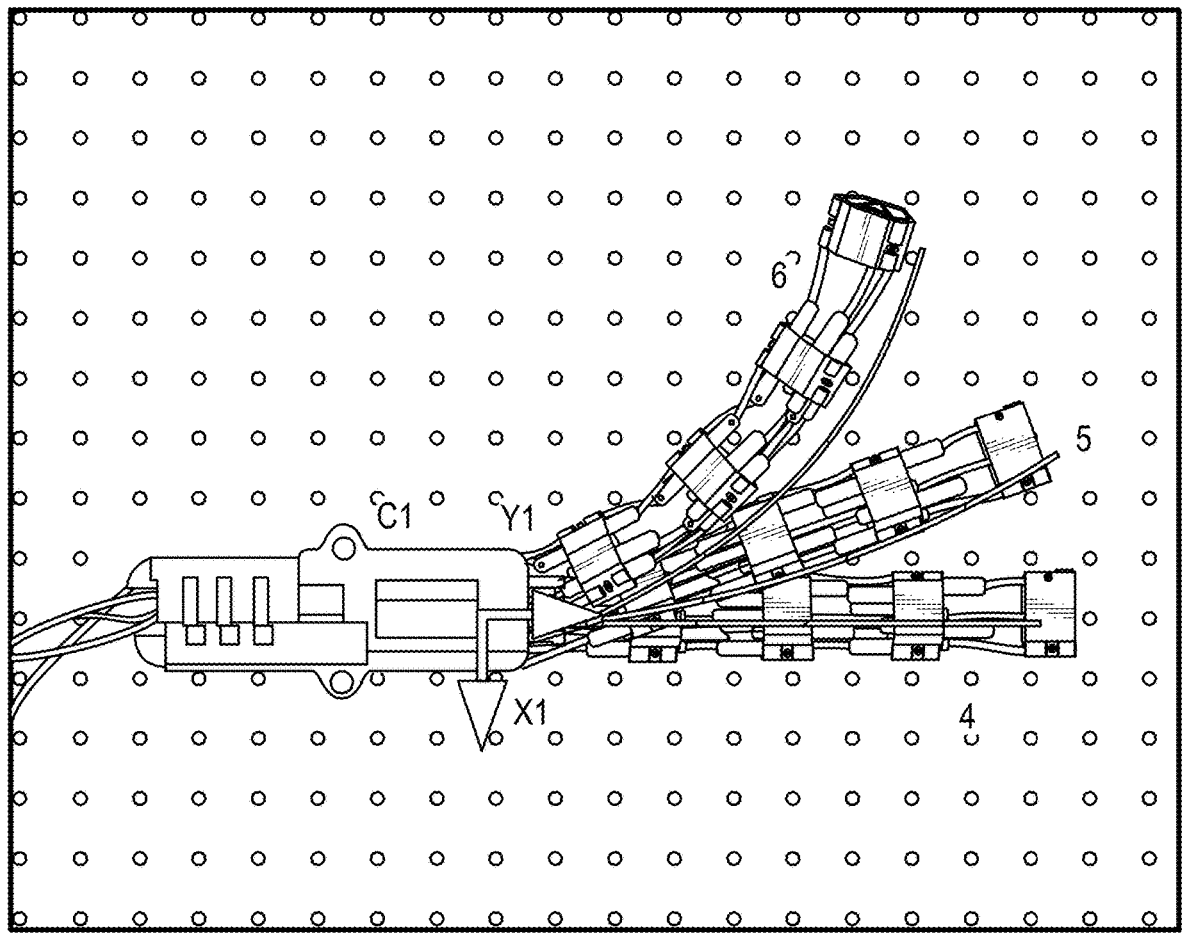

Although the prototype demonstrates good bending shapes as a whole, the first subsegment 108a was observed to have larger bending angles than the rest. This is partially due to the non-uniform motion effect discussed above. Additionally, the non-uniformity for the first subsegment 108a comes from its large driving force. For instance, the manipulator mechanism described herein utilizes propagation to transmit motion from the base to the most distal ones of the subsegments 108n. From conservation of energy, it is understood that motion will accumulate and amplify the driving force from each subsegment 108 onto the first subsegment 102a, which causes its flexible rods 122 to deform more than that of other subsegments 108. This observation suggests that a more accurate statics-based kinematic model may be employed to calculate the manipulator shape. FIGS. 17A and 17B further illustrate the spatial bending and the extensibility of the robotic system 100.

According to various embodiments, by leveraging the rigid coupling hybrid mechanism and the flexible parallel mechanisms, a three DoF continuum manipulator 104 with spatial bending (2R) and one axial extension (1T) mobility is described. Generally, the motion of the i-th link drives the (i+1)-th link so that local motion may be copied and propagated from a first subsegment 108a (e.g., a base subsegment 108) to a tip subsegment 108n. Flexible parallel mechanisms may be employed to realize basic 2R1T subsegment motion, and rack-and-pinion sets 118 are employed to couple adjacent subsegments 108. To this effect, the 2R1T motion is copied by each subsegment 108 and the continuum manipulator 104 achieves spatial bending and extension mobility. To calculate the configuration of this the robotic system 100 described herein, a simplified kinematic model is described. Workspace analysis was also carried out to evaluate the capability of the robotic system 100. A small prototype was manufactured to verify proposed mobility. Preliminary tests showed that the robotic system 100 described herein is able to extend 32% of its original length and bend over 80 degrees. It is understood that these parameters may change based on a difference in materials, number of subsegments 108, and so forth. However, the kinematic model described herein provides an estimation of an actual shape of the robotic system 100, which ignores static (which can be more approximated by a spline instead of an arc).

Figure 18:
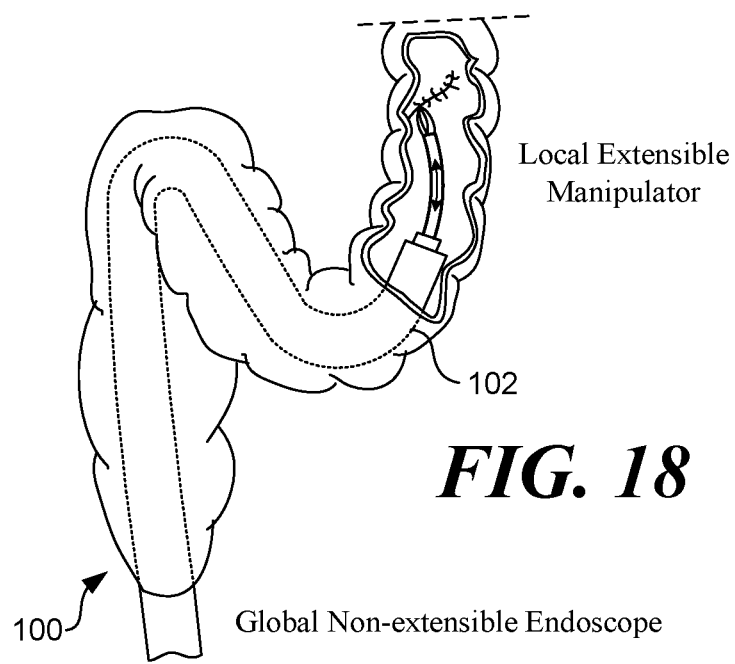
FIG. 18 shows an example implementation of the robotic system having the extensible continuum manipulator in an endoscopy medical procedure according to various embodiments of the present disclosure.

Referring to FIG. 18, an example implementation of the robotic system 100 is shown. The ability of the continuum manipulator to deform and extend may provide use in endoscopies or similar medical procedures. For instance, an end effector may include a biopsy device configured to collect tissue from a sample site, while the continuum manipulator 104 can deform to the shape of a colon or other body cavity having a non-uniform path to the sample site.

The features, structures, or characteristics described above can be combined in one or more embodiments in any suitable manner. If possible, the features discussed in the embodiments are interchangeable. In the description above, various details are provided to give a sufficient understanding of the embodiments of the present disclosure. However, it is understood that the technical implementations of the present disclosure can be practiced without one or more of the specific details, and/or other methods, components, materials, etc. can be used. In other cases, well-known structures (e.g., end effectors), materials, or operations are not shown or described in detail to avoid obscuring aspects of the present disclosure.

Although relative terms such as "upper" and "lower" are used in this specification to describe the relative relationship between one component of an icon and another component of an icon, these terms are used in this specification only for explanatory purposes. For example, according to the direction of the example described in the drawings, it can be understood that if the component of a label is turned upside down, the component described as "upper" will become the "lower" component. Other relative terms, such as "high," "low," "top,", and "bottom" have similar meanings. When a structure is "on" another structure, it may mean that a certain structure is integrally formed on another structure, or that a certain structure is "directly" arranged on another structure, or that a certain structure is "indirectly" installed on another structure through the other structure.

In this specification, the terms "a," "an," "the," "said," and "at least one" are used to indicate that there are one or more elements, components, etc. The terms "includes," "including," and "having" are used to mean open-ended inclusion and may indicate that, in addition to the listed elements, components, etc., there may be additional elements, components, etc. The terms "first," "second," "third," and so forth are intended only as labels, and are not a limitation on the number of objects. It is understood that, if multiple components are described above, the components may be specifically enumerated in the claims using "first," "second," "third," and so forth.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Clause 1. A system, comprising: at least one actuator; and a continuum manipulator comprising an extensible continuum manipulator (ECM) body, the extensible continuum manipulator body comprising: a plurality of subsegments serially connected to one another, a proximal one of the plurality of subsegments being coupled to the at least one actuator; wherein adjacent ones of the plurality of subsegments are coupled to one another using a coupling arrangement such that, when moved by the at least one actuator, the proximal one of the plurality of subsegments propagates subsegment motion to distal ones of the plurality of subsegments.

Clause 2. The system of clause 1, wherein: the at least one actuator is a plurality of linear actuators; the proximal one of the plurality of subsegments comprises a plurality of rack-and-pinion sets each comprising a first rack coupled to a respective one of the plurality of linear actuators, a second rack coupled to a body of the proximal one of the plurality of subsegments, and a pinion rotatably coupled to and positioned between the first rack and the second rack; and the plurality of rack-and-pinion sets are coupled to the plurality of linear actuators such that lateral force provided by the plurality of linear actuators causes the first rack of the plurality of rack-and-pinion sets to shift relative to the second rack through rotation of the pinion.

Clause 3. The system of any of clauses 1-2, wherein: the coupling arrangement comprises a rack-and-pinion transmission set coupling the adjacent ones of the plurality of subsegments; and the adjacent ones of the plurality of subsegments comprise a first subsegment and a second subsegment coupled to one another by a multi-chain parallel mechanism, the multi-chain parallel mechanism comprising a plurality of rods.

Clause 4. The system of any of clauses 1-3, wherein: the first subsegment comprises a first plurality of rack-and-pinion sets coupled to proximal ends of a first portion of the plurality of rods; distal ends of the first portion of the plurality of rods are coupled to a body of the second subsegment; the second subsegment comprises a second plurality of rack-and-pinion sets coupled to distal ends of a second portion of the plurality of rods; and proximal ends of the second portion of the plurality of rods are coupled to a body of the first subsegment.

Clause 5. The system of any of clauses 1-4, wherein: the first plurality of rack-and-pinion sets comprises a first rack set having a rack coupled to a proximal end of a first one of the rods, a second rack set having a rack coupled to a proximal end of a second one of the rods, and a third rack set having a rack coupled to a proximal end of a third one of the rods; a distal end of the first one of the rods, a distal end of the second one of the rods, and a distal end of the third one of the rods are coupled to the body of the second subsegment; the second plurality of rack-and-pinion sets comprises a first rack set having a rack coupled to a distal end of a fourth one of the rods, a second rack set having a rack coupled to a distal end of a fifth one of the rods, and a third rack set having a rack coupled to a distal end of a sixth one of the rods; and a proximal end of the fourth one of the rods, a proximal end of the fifth one of the rods, and a proximal end of the sixth one of the rods are coupled to the body of the first subsegment.

Clause 6. The system of any of clauses 1-5, wherein: the first one of the rods, the second one of the rods, and the third one of the rods are driving rods configured to induce motion in the second subsegment; and the fourth one of the rods, the fifth one of the rods, and the sixth one of the rods are measuring rods configured to measure motion generated by the first subsegment.

Clause 7. The system of any of clauses 1-6, wherein: individual ones of the plurality of rods are flexible; and the coupling arrangement is configured to provide at least two decoupled and independent rotations with respect to perpendicular axes and at least one independent axial extension.

Clause 8. The system of any of clauses 1-7, wherein individual ones of the plurality of rods are rigid and comprise at least one joint selected from a group consisting of: a prismatic joint, a revolute joint, and a spherical joint.

Clause 9. The system of any of clauses 1-8, further comprising a controller comprising processing circuitry configured to control motion of the extensible continuum manipulator body in at least a 3 degrees-of-freedom (3DoF) manner.

Clause 10. The system of any of clauses 1-9, wherein: a number of the plurality of subsegments is two to ten; the at least one actuator is a plurality of linear actuators; and a number of the plurality of linear actuators is three.

Clause 11. A method, comprising: providing at least one actuator; providing a continuum manipulator comprising an extensible continuum manipulator (ECM) body, the extensible continuum manipulator body comprising: a plurality of subsegments serially connected to one another, a proximal one of the plurality of subsegments being coupled to the at least one actuator; wherein adjacent ones of the plurality of subsegments are coupled to one another using a coupling arrangement such that, when moved by the at least one actuator, the proximal one of the plurality of subsegments propagates subsegment motion to distal ones of the plurality of subsegments; and directing, by a controller, movement of the continuum manipulator in a three-dimensional space, wherein the movement comprises adjusting a curvature of the extensible continuum manipulator body and adjusting an extension of the extensible continuum manipulator body in a lateral direction relative to a longitudinal axis of the extensible continuum manipulator body.

Clause 12. The method of clause 11, wherein: the at least one actuator is a plurality of linear actuators; the proximal one of the plurality of subsegments comprises a plurality of rack-and-pinion sets each comprising a first rack coupled to a respective one of the plurality of linear actuators, a second rack coupled to a body of the proximal one of the plurality of subsegments, and a pinion rotatably coupled to and positioned between the first rack and the second rack; and the plurality of rack-and-pinion sets are coupled to the plurality of linear actuators such that lateral force provided by the plurality of linear actuators causes the first rack of the plurality of rack-and-pinion sets to shift relative to the second rack through rotation of the pinion.

Clause 13. The method of any of clauses 11-12, wherein: the coupling arrangement comprises a rack-and-pinion transmission set coupling the adjacent ones of the plurality of subsegments; and the adjacent ones of the plurality of subsegments comprise a first subsegment and a second subsegment coupled to one another by a multi-chain parallel mechanism, the multi-chain parallel mechanism comprising a plurality of rods.

Clause 14. The method of any of clauses 11-13, wherein: the first subsegment comprises a first plurality of rack-and-pinion sets coupled to proximal ends of a first portion of the plurality of rods; distal ends of the first portion of the plurality of rods are coupled to a body of the second subsegment; the second subsegment comprises a second plurality of rack-and-pinion sets coupled to distal ends of a second portion of the plurality of rods; and proximal ends of the second portion of the plurality of rods are coupled to a body of the first subsegment.

Clause 15. The method of any of clauses 11-14, wherein: the first plurality of rack-and-pinion sets comprises a first rack set having a rack coupled to a proximal end of a first one of the rods, a second rack set having a rack coupled to a proximal end of a second one of the rods, and a third rack set having a rack coupled to a proximal end of a third one of the rods; a distal end of the first one of the rods, a distal end of the second one of the rods, and a distal end of the third one of the rods are coupled to the body of the second subsegment; the second plurality of rack-and-pinion sets comprises a first rack set having a rack coupled to a distal end of a fourth one of the rods, a second rack set having a rack coupled to a distal end of a fifth one of the rods, and a third rack set having a rack coupled to a distal end of a sixth one of the rods; and a proximal end of the fourth one of the rods, a proximal end of the fifth one of the rods, and a proximal end of the sixth one of the rods are coupled to the body of the first subsegment.

Clause 16. The method of any of clauses 11-15, wherein: the first one of the rods, the second one of the rods, and the third one of the rods are driving rods configured to induce motion in the second subsegment; and the fourth one of the rods, the fifth one of the rods, and the sixth one of the rods are measuring rods configured to measure motion generated by the first subsegment.

Clause 17. The method of any of clauses 11-16, wherein: individual ones of the plurality of rods are flexible; and the coupling arrangement is configured to provide at least two decoupled and independent rotations with respect to perpendicular axes and at least one independent axial extension.

Clause 18. The method of any of clauses 11-17, wherein individual ones of the plurality of rods are rigid and comprise at least one joint selected from a group consisting of: a prismatic joint, a revolute joint, and a spherical joint.

Clause 19. The method of any of clauses 11-18, wherein: a number of the plurality of subsegments is two to ten; the at least one actuator is a plurality of linear actuators; and a number of the plurality of linear actuators is three.

Clause 20. The method of any of clauses 11-19, wherein directing, by the controller, the movement of the continuum manipulator in the three-dimensional space comprises: modeling, by the controller, kinematics of the extensible continuum manipulator body in the three-dimensional space; and controlling, by the controller, the movement of the extensible continuum manipulator body in the three-dimensional space based at least in part on the kinematics as modeled.

Therefore, the following is claimed:

1. A system, comprising:
   at least one actuator; and
   a continuum manipulator comprising an extensible continuum manipulator (ECM) body, the extensible continuum manipulator body comprising:
      a plurality of subsegments serially connected to one another, a proximal one of the plurality of subsegments being coupled to the at least one actuator;
      wherein adjacent ones of the plurality of subsegments are coupled to one another using a coupling arrangement such that, when moved by the at least one actuator, the proximal one of the plurality of subsegments propagates subsegment motion to distal ones of the plurality of subsegments; and
      wherein the coupling arrangement is configured to provide at least two decoupled and independent rotations with respect to perpendicular axes and at least one independent axial extension.

2. The system of claim 1, wherein:
   the at least one actuator is a plurality of linear actuators;
   the proximal one of the plurality of subsegments comprises a plurality of rack-and-pinion sets each comprising a first rack coupled to a respective one of the plurality of linear actuators, a second rack coupled to a body of the proximal one of the plurality of subsegments, and a pinion rotatably coupled to and positioned between the first rack and the second rack; and
   the plurality of rack-and-pinion sets are coupled to the plurality of linear actuators such that lateral force provided by the plurality of linear actuators causes the first rack of the plurality of rack-and-pinion sets to shift relative to the second rack through rotation of the pinion.

3. The system of claim 1, wherein:
the coupling arrangement comprises a rack-and-pinion transmission set coupling the adjacent ones of the plurality of subsegments; and
the adjacent ones of the plurality of subsegments comprise a first subsegment and a second subsegment coupled to one another by a multi-chain parallel mechanism, the multi-chain parallel mechanism comprising a plurality of rods.

4. The system of claim 3, wherein:
the first subsegment comprises a first plurality of rack-and-pinion sets coupled to proximal ends of a first portion of the plurality of rods;
distal ends of the first portion of the plurality of rods are coupled to a body of the second subsegment;
the second subsegment comprises a second plurality of rack-and-pinion sets coupled to distal ends of a second portion of the plurality of rods; and
proximal ends of the second portion of the plurality of rods are coupled to a body of the first subsegment.

5. The system of claim 4, wherein:
the first plurality of rack-and-pinion sets comprises a first rack set having a rack coupled to a proximal end of a first one of the rods, a second rack set having a rack coupled to a proximal end of a second one of the rods, and a third rack set having a rack coupled to a proximal end of a third one of the rods;
a distal end of the first one of the rods, a distal end of the second one of the rods, and a distal end of the third one of the rods are coupled to the body of the second subsegment;
the second plurality of rack-and-pinion sets comprises a first rack set having a rack coupled to a distal end of a fourth one of the rods, a second rack set having a rack coupled to a distal end of a fifth one of the rods, and a third rack set having a rack coupled to a distal end of a sixth one of the rods; and
a proximal end of the fourth one of the rods, a proximal end of the fifth one of the rods, and a proximal end of the sixth one of the rods are coupled to the body of the first subsegment.

6. The system of claim 5, wherein:
the first one of the rods, the second one of the rods, and the third one of the rods are driving rods configured to induce motion in the second subsegment; and
the fourth one of the rods, the fifth one of the rods, and the sixth one of the rods are measuring rods configured to measure motion generated by the first subsegment.

7. The system of claim 4, wherein:
individual ones of the plurality of rods are flexible.

8. The system of claim 4, wherein individual ones of the plurality of rods are rigid and comprise at least one joint selected from a group consisting of: a prismatic joint, a revolute joint, and a spherical joint.

9. The system of claim 1, further comprising a controller comprising processing circuitry configured to control motion of the extensible continuum manipulator body in at least a 3 degrees-of-freedom (3DoF) manner.

10. The system of claim 1, wherein: a number of the plurality of subsegments is two to ten; the at least one actuator is a plurality of linear actuators; and a number of the plurality of linear actuators is three.

11. A method, comprising:
providing at least one actuator;
providing a continuum manipulator comprising an extensible continuum manipulator (ECM) body, the extensible continuum manipulator body comprising:
a plurality of subsegments serially connected to one another, a proximal one of the plurality of subsegments being coupled to the at least one actuator;
wherein adjacent ones of the plurality of subsegments are coupled to one another using a coupling arrangement such that, when moved by the at least one actuator, the proximal one of the plurality of subsegments propagates subsegment motion to distal ones of the plurality of subsegments;
wherein the coupling arrangement is configured to provide at least two decoupled and independent rotations with respect to perpendicular axes and at least one independent axial extension; and
directing, by a controller, movement of the continuum manipulator in a three-dimensional space, wherein the movement comprises adjusting a curvature of the extensible continuum manipulator body and adjusting an extension of the extensible continuum manipulator body in a lateral direction relative to a longitudinal axis of the extensible continuum manipulator body.

12. The method of claim 11, wherein:
the at least one actuator is a plurality of linear actuators;
the proximal one of the plurality of subsegments comprises a plurality of rack-and-pinion sets each comprising a first rack coupled to a respective one of the plurality of linear actuators, a second rack coupled to a body of the proximal one of the plurality of subsegments, and a pinion rotatably coupled to and positioned between the first rack and the second rack; and
the plurality of rack-and-pinion sets are coupled to the plurality of linear actuators such that lateral force provided by the plurality of linear actuators causes the first rack of the plurality of rack-and-pinion sets to shift relative to the second rack through rotation of the pinion.

13. The method of claim 11, wherein:
the coupling arrangement comprises a rack-and-pinion transmission set coupling the adjacent ones of the plurality of subsegments; and
the adjacent ones of the plurality of subsegments comprise a first subsegment and a second subsegment coupled to one another by a multi-chain parallel mechanism, the multi-chain parallel mechanism comprising a plurality of rods.

14. The method of claim 13, wherein:
the first subsegment comprises a first plurality of rack-and-pinion sets coupled to proximal ends of a first portion of the plurality of rods;
distal ends of the first portion of the plurality of rods are coupled to a body of the second subsegment;
the second subsegment comprises a second plurality of rack-and-pinion sets coupled to distal ends of a second portion of the plurality of rods; and
proximal ends of the second portion of the plurality of rods are coupled to a body of the first subsegment.

15. The method of claim 14, wherein:
the first plurality of rack-and-pinion sets comprises a first rack set having a rack coupled to a proximal end of a first one of the rods, a second rack set having a rack coupled to a proximal end of a second one of the rods, and a third rack set having a rack coupled to a proximal end of a third one of the rods;

a distal end of the first one of the rods, a distal end of the second one of the rods, and a distal end of the third one of the rods are coupled to the body of the second subsegment;

the second plurality of rack-and-pinion sets comprises a first rack set having a rack coupled to a distal end of a fourth one of the rods, a second rack set having a rack coupled to a distal end of a fifth one of the rods, and a third rack set having a rack coupled to a distal end of a sixth one of the rods; and a proximal end of the fourth one of the rods, a proximal end of the fifth one of the rods, and a proximal end of the sixth one of the rods are coupled to the body of the first subsegment.

16. The method of claim 15, wherein:

the first one of the rods, the second one of the rods, and the third one of the rods are driving rods configured to induce motion in the second subsegment; and the fourth one of the rods, the fifth one of the rods, and the sixth one of the rods are measuring rods configured to measure motion generated by the first subsegment.

17. The method of claim 14, wherein:
individual ones of the plurality of rods are flexible.

18. The method of claim 14, wherein individual ones of the plurality of rods are rigid and comprise at least one joint selected from a group consisting of: a prismatic joint, a revolute joint, and a spherical joint.

19. The method of claim 11, wherein: a number of the plurality of subsegments is two to ten; the at least one actuator is a plurality of linear actuators; and a number of the plurality of linear actuators is three.

20. The method of claim 11, wherein directing, by the controller, the movement of the continuum manipulator in the three-dimensional space comprises:

modeling, by the controller, kinematics of the extensible continuum manipulator body in the three-dimensional space; and controlling, by the controller, the movement of the extensible continuum manipulator body in the three-dimensional space based at least in part on the kinematics as modeled.

* * * * *